United States Patent [19]

Metzger et al.

[11] Patent Number: 5,665,347

[45] Date of Patent: Sep. 9, 1997

[54] IL-12 INHIBITION OF B1 CELL ACTIVITY

[75] Inventors: Dennis W. Metzger, Sylvania, Ohio; Victor H. Van Cleave, Londonderry, N.H.

[73] Assignees: Genetics Institute, Cambridge, Mass.; Medical College of Ohio, Toledo, Ohio

[21] Appl. No.: 382,658

[22] Filed: Feb. 2, 1995

[51] Int. Cl.$^6$ .......................... A61K 38/20; A61K 45/05
[52] U.S. Cl. .......................... 424/85.2; 514/12; 514/21
[58] Field of Search ........................... 424/85.1, 85.2; 530/351; 514/2, 12, 21

[56] References Cited

FOREIGN PATENT DOCUMENTS

A4315127  11/1994  Germany.

OTHER PUBLICATIONS

Via, C.S., et al., "IL12 Prevents Autoimmunity in a Murine Model of SLE", *Arthritis and Rheumatism*, 36(9):S63, NY, NY (1993) (Abstract).

Palanivel, V., et al., "Recombinant Murine IL–12 Inhibits Ligand–Specific Recruitment of Peritoneal B220+, CD5+ (B–1) Cells", *J. of Immunology*, 152(6):3220, Baltimore, MD, USA (15 Mar. 1995) (Abstract).

Jamin, C., et al., "Expression of CD5 and CD72 on T and B Cell Subsets in Rheumatoid Arthritis and Sjoegren's Syndrome", *Clin. Exp. Immunology*, 92(2):245–250 (1993).

Stall, A.M., et al., "LY–1 B–Cell Clones Similar to Human Chronic Lymphocytic Leukemias Routinely Develop in Older Normal Mice and Young Autoimmune (New Zealand Black–Related) Animals)", *PNAS, USA*, 85:7312–7316 (1988).

Chizzonite, R., et al., "Initial Characterization of the IL–12 Receptor (IL–12R) on Concanavalin–A Activated Mouse Spenocytes", *J. Cell Biochemistry, Suppl.*, 0(17) Part B:73, NY, NY (1993).

Metzger, D.W., et al., "The Effects of IL12 on B–Cell Subset Function", *Research in Immunology*, 146(7–8):499–505, Paris, France (1995).

Vogel, L.A., et al., "Inhibition of Murine B1 Lymphocytes by Interleukin–12", *Eur. J. of Immunology*, 26(1):219–223, Weinheim, DE (1996).

Leonard, J.P., et al., "Prevention of Experimental Autoimmune Encephalomyelitis by Antibodies Against Interleukin 12", *J. Exp. Med.*, 181(1):381–386 (1995).

McKnight, A.J., "Effects of IL–12 on helper T cell–dependent immune responses in vivo", *J. Immunol.*, 152:2172–2179 (1994).

Li, L., et al., "Recombinant human natural killer cell stimulating factor is a human B cell growth factor", *Faseb J.*, 5:A1090 (1991) (Abstract).

Jelinek, D.F. and Braaten, J.K., "Role of IL–12 in human B lymphocyte proliferation and differentiation", *J. of Immunol.*, 154:1606–1613 (1995).

Kiniwa, M., et al., "Recombinant Interleukin–12 Suppresses the Synthesis of Immunoglobulin E by Interleukin–4 Stimulated Human Lymphocytes", *J. Clin. Invest.*, 90:262–266 (Jul. 1992).

(List continued on next page.)

*Primary Examiner*—Ponnathapura Achutamurthy
*Attorney, Agent, or Firm*—Hamilton, Brook, Smith & Reynolds, P.C.

[57] ABSTRACT

The invention relates to a method of suppressing B1 cell activity in a host (e.g., mammalian, including human) comprising administering to the host an effective amount of IL-12 that significantly suppresses or inhibits B1 cell activity. In addition, the invention relates to a method of treating a B1 cell disorder in a host, comprising administering to the host an effective therapeutic amount of IL-12. The invention further encompasses a method of screening for substances (e.g., proteins, peptides, small molecules) which enhance or suppress the inhibition of B1 cell activity by IL-12. The invention also relates to a substance identified by the methods of screening for a substance which enhances or suppresses IL-12 inhibition of B1 cell activity.

7 Claims, 18 Drawing Sheets

OTHER PUBLICATIONS

Trinchieri, G., "Interleukin-12: A Cytokine Produced by Antigen-Presenting Cells With Immunoregulatory Functions in the Generation of T-Helper Cells Type 1 and Cytotoxic Lymphocytes", *Blood*, 84(12):4008–4027 (Dec. 15, 1994).

Morris, S.C., et al., "Effects of IL-12 on in Vivo Cytokine Gene Expression and Ig Isotype Selection", *J. of Immunol.*, 152:1047–1056 (1994).

Desai, B.B., et al., "Il-12 Receptor", *J. of Immunol.*, 148(10):3125–3132 (May 15, 1992).

Gemmell et al: 'Cytokines and T Cell Switching', Critical Reviews in Oral Biology and Medicine, vol. 5(314), pp. 249–279, 1994.

IL-12 INHIBITION OF B1 CELL ACTIVITY

BACKGROUND

B1 cells play an important role in the development of autoimmunity and lymphoid malignancy (Youinou, P. et al., *Eur. J. of Clin. Invest.*, 23:139–150 (1993). B1 cells can be identified by the presence of small amounts of the pan-T cell marker, CD5, in conjunction with the typical B cell markers IgM, CD45R(B220), class II MHC, and FcγR. However, they lack T cell markers such as CD3, CD4, and CD8. They also appear to be the B cell population that expresses the receptor for IL-5.

In humans, B1 cells are increased in frequency in many autoimmune conditions and are responsible for production of autoantibodies such as IgM rheumatoid factor. (Lydyard, P.M., et al., *Immunol. Today*, 8:37–38 (1987); Mix, E., et al., *Clin. Exp. Immunol.*, 79:21–27 (1990); Munoz, A., et al., *Clin. Exp. Immunol.*, 83:304–308 (1991); Mizutani, H., et al., *Br. J. Haematol.*, 78:474–479 (1991); Jarvis, J. N., et al., *Arthritis Rheum.*, 35:204–207 (1992); Hardy, R. R., et al., *Science*, 236:81–83 (1987)). In mice, B1 cells have been found to be the primary source of autoantibodies found in normal mice and autoimmune strains of mice, such as the NZBWF$_1$ mouse strain (Hayakawa, K., et al., *Proc. Natl. Acad. Sci, USA*, 81:2494–2498 (1984); Hayakawa, K., et al., *J. Exp. Med.*, 157:202–218 (1983); Stall, A. M., et al., *Proc. Natl. Acad. Sci, USA*, 85:7312–7316 (1988)).

In addition, B1 cells also appear to be the B cells responsible for chronic lymphocytic leukemia (CLL), the most common adult leukemia in Western societies and a malignancy often associated with autoimmunity. Approximately 95% of patients with CLL have leukemic cells that coexpress CD5 in conjunction with other B cell surface antigens (Royston, I., et al., *J. Immunol.*, 125:725–731 (1980); Boumsell, L., et al., *J. Exp. Med.*, 152:229–234 (1980)). This phenotype is not present on immature B lymphocytes in bone marrow nor on other "immature" B cell malignancies. Furthermore, unlike other leukemias, normal and leukemic B1 cells can express myeloid-associated markers such as CD11b, CD14, and CD15 (Morabito, F., et al., *Blood*, 70:1750–1757 (1987)). Murine B1 cells show increased longevity in vitro and often give rise to B cell lymphomas in aged mice (Braun, J., *J. Immunol.*, 130:2113–2116 (1983); Lanier, L. L., et al., *Immunogenetics*, 16:367–371 (1982); Davidson, W. F., et al., *J. Immunol.*, 133:744–753 (1984); Pennell, C. A., et al., *Proc. Natl. Acad. Sci, USA*, 82:3799–3803 (1985)).

Treatment of these B1 cell disorders generally involves the use of corticosteroids for autoimmune diseases and immunosuppressive chemotherapy and irradiation for CLL. These current treatments of B1 cell disorders are non-specific and result in a general suppression of a host's immune system.

SUMMARY OF THE INVENTION

The present invention is based on the surprising discoveries that interleukin-12 (IL-12) inhibits the functional activity of B1 cells, but not B2 cells, and that B1 cells and activated splenic B cells possess an IL-12 receptor. Based on these discoveries, it has been demonstrated that IL-12 can be used to suppress B1 cell activity, and thus, treat B1 cell disorders. In one embodiment, the invention relates to a method of suppressing B1 cell activity in a host (e.g., mammalian, including human) comprising administering to the host an effective amount of IL-12 that significantly suppresses or inhibits B1 cell activity.

In another embodiment, the present invention relates to a method of treating a B1 cell disorder in a host, comprising administering to the host an effective therapeutic amount of IL-12. B1 cell disorders include or are associated with chronic lymphocytic leukemia (CLL), hairy cell leukemia, prolymphocytic leukemia, well differentiated lymphocytic lymphomas, infectious mononucleosis, human immunodeficiency virus, schizophrenia and autoimmune diseases, such as systemic lupus erythematosus (SLE), rheumatoid arthritis, multiple sclerosis, immune thrombocytopenia purpura, primary Sjogren's syndrome, juvenile arthritis, primary antiphospholipid syndrome, Graves' disease, myasthenia gravis, chronic hepatitis, Crohn's disease and type 1 diabetes.

The invention further encompasses a method of screening for substances (e.g., proteins, peptides, small molecules) which enhance or inhibit the inhibition of B1 cell activity by IL-12.

Thus, IL-12 plays a central role in the regulation of both innate and specific cell-mediated immunity and as shown herein, has important consequences for B1 cell function. The present invention provides for a specific treatment of B1 cell disorders using IL-12 which specifically suppresses the activity of B1 cell activity.

DETAILED DESCRIPTION OF THE INVENTION

Figure 1A:
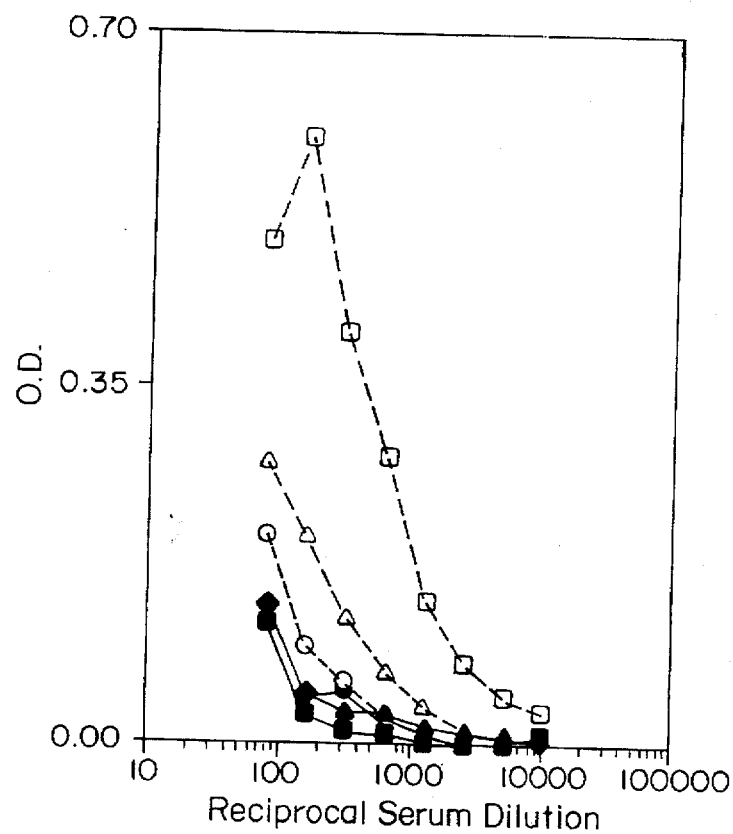
FIGS. 1A–1D are graphs of the reciprocal serum dilution versus optical density (OD) at 405 nm demonstrating suppression of the IgG1 and enhancement of the IgG2a anti-phosphorylcholine (anti-PC) response after IL-12 treatment (solid lines indicate mice receiving IL-12 and dashed lines indicate mice receiving phosphate buffered saline (PBS)).

The present invention relates to a method of suppressing B1 cell activity in a host (e.g., mammalian), comprising administering to the host an effective amount of interleukin-12 (IL-12). In one embodiment, the invention relates to a method of treating a B1 cell disorder in a host, comprising administering to the host an effective amount of IL-12. B1 cell disorders which can be treated using the method of the present invention include chronic lymphocytic leukemia (CLL) hairy cell leukemia, prolymphocytic leukemia, well differentiated lymphocytic lymphomas, human immunodeficiency virus, infectious mononucleosis, schizophrenia and autoimmune diseases, such as systemic lupus erythematosus (SLE), rheumatoid arthritis, multiple sclerosis, immune thrombocytopenia purpura, primary Sjogren's syndrome, juvenile arthritis, primary antiphospholipid syndrome, Graves' disease, myasthenia gravis, chronic hepatitis, Crohn's disease and type 1 diabetes.

Another embodiment of the present invention is a method of screening for substances (e.g., proteins, peptides, small molecules) which suppress or enhance the inhibition of B1 cell activity by IL-12. In one embodiment, the ability of a substance to suppress IL-12 inhibition of B1 cells is assessed, wherein the substance is combined with cultured B1 cells and IL-12, under conditions appropriate for IL-12 inhibition of B1 cells. Activation of B1 cell activity is an indication that the substance suppresses or interferes with IL-12 inhibition of B1 cell activity. Therefore, substances such as antibodies to IL-12, peptides, peptidomimatics, other small molecules or antibodies to the B cell IL-12 receptor can be assessed for their ability to inhibit the IL-12 inhibition of B1 cell activity. In another embodiment, the ability of a substance to enhance IL-12 inhibition of B1 cell activity is assessed wherein the substance is combined with cultured B1 cells and IL-12, under conditions appropriate for IL-12 inhibition of B1 cells. Further inhibition of B1 cell activity is an indication that the substance enhances IL-12 inhibition of B1 cell activity. Measurement of the ability of a substance to suppress or enhance the inhibition of B1 cell activity by IL-12 B1 is accomplished by comparing the results to those obtained with an appropriate control (i.e., the same reagents as used to assess the substance except the substance is not present). The present invention also relates to a substance identified by the methods for assessing the ability of a substance to suppress or enhance the inhibition of B1 cell activity by IL-12.

IL-12 is a recently characterized heterodimeric cytokine that has a molecular weight of 75 kDa and is composed of disulfide-bonded 40 kDa and 35 kDa subunits. It is produced by macrophages and B cells, and binds to receptors on activated T cells and NK cells. It has several effects including 1) enhanced proliferation of T cells and NK cells, 2) increased cytolytic activities of T cells, NK cells, and macrophages, 3) induction of IFN-γ production and to a lesser extent, TNF-α and GM-CSF, and 4) activation of TH1 cells (Trinchieri, G., et al., *Blood*, 84:4008–4027 (1994). IL-12 has been shown to be an important costimulator of proliferation in Th1 clones (Kennedy et al., *Eur. J. Immunol.* 24:2271–2278, 1994) and leads to increased production of IgG2a antibodies in serum (Morris, S. C., et al., *J. Immunol.* 152:1047 (1994). Administration of IL-12 also decreases production of IgG1 antibodies (Morris, S. C., et al., *J. Immunol.* 152:1047 (1994); McKnight, A. J., *J. Immunol.* 152:2172 (1994)), indicating suppression of the Th2 response. The purification and cloning of IL-12 are disclosed in PCT publication nos. WO 92/05256 and WO 90/05147, and in European patent publication no. 322,827 (identified as "CLMF").

As used herein, "interleukin-12" and "IL-12" refer to interleukin 12, its individual subunits, multimers of its individual subunits, fragments thereof which exhibit B1 cell suppression or inhibition activity and functional equivalents and/or analogues of "interleukin-12" and "IL-12". Functional equivalents of "interleukin-12" and "IL-12" include modified IL-12 protein such that the resulting IL-12 product has activity similar to the IL-12 described herein, and nucleic acid sequences which through the degeneracy of the genetic code encode a similar peptide gene product as IL-12 and having the IL-12 activity described herein. For example, a functional equivalent of "interleukin-12" and "IL-12" can contain a "silent" codon or amino acid substitution (e.g., substitution of one acidic amino acid for another acidic amino acid; or substitution of one codon encoding a hydrophobic amino acid for another codon encoding a hydrophobic amino acid).

IL-12 suitable for use with the present invention can be obtained from a variety of sources or synthesized. For example, IL-12 can be purified from natural sources (e.g., human, animal), produced by chemical synthesis or produced by recombinant DNA techniques as discussed in Example 1. In addition, the IL-12 for use with the present invention includes nucleic acid sequences encoding IL-12, as well as the RNAs.

In the method of the present invention, an effective amount of IL-12 that significantly inhibits or suppress B1 cell activity is administered. In addition, the IL-12 can be administered either before or after a B1 cell disorder has manifested in a host. Thus, the IL-12 can be administered to a host who either exhibits the disease state caused by B1 cell activity or does not yet exhibit the disease state caused by B1 cell activity. Thus, the IL-12 can be administered to hosts either before or after the disease state is manifested in the host and can result in prevention, amelioration, elimination or a delay in the onset of the disease state caused by the B1 cell activity.

The IL-12 can be administered to a host in a variety of ways. The routes of administration include intradermal, transdermal (e.g., slow release polymers), intramuscular, intraperitoneal, intravenous, subcutaneous, oral, epidural and intranasal routes. Any other convenient route of administration can be used, for example, infusion or bolus injection, or absorption through epithelial or mucocutaneous linings. In addition, the IL-12 can be administered together with other components or biologically active agents, such as pharmaceutically acceptable surfactants (e.g., glycerides), excipients (e.g., lactose), carriers, diluents and vehicles. If desired, certain sweetening, flavoring and/or coloring agents can also be added.

Further, IL-12 can be administered by in vivo expression of polynucleotides encoding such into a mammalian subject. For example, the IL-12 can be administered to a host using a live vector, wherein the live vector containing IL-12 nucleic acid sequences is administered under conditions in which the IL-12 is expressed in vivo.

Several expression vector systems are available commercially or can be reproduced according to recombinant DNA and cell culture techniques. For example, vector systems such as the yeast or vaccinia virus expression systems, or virus vectors can be used in the methods and compositions of the present invention (Kaufman, R. J., *A J. of Meth. in Cell and Molec. Biol.*, 2:221–236 (1990)). Other techniques using naked plasmids or DNA, and cloned genes encapsulated in targeted liposomes or in erythrocyte ghosts, can be used to introduce IL-12 polynucleotides into the host (Freidman, T., *Science*, 244:1275–1281 (199); Rabinovich, N. R., et al., *Science*, 265:1401–1404 (1994)). The construction of expression vectors and the transfer of vectors and nucleic acids into various host cells can be accomplished using genetic engineering techniques, as described in manuals like *Molecular Cloning and Current Protocols in Molecular Biology*, which are hereby incorporated by reference, or by using commercially available kits (Sambrook, J., et al., *Molecular Cloning*, Cold Spring Harbor Press, 1989; Ausubel, F. M., et al., *Current Protocols in Molecular Biology*, Greene Publishing Associates and Wiley-Interscience, 1989).

An effective amount of IL-12 is administered in the methods of the present invention which is an amount that produces significant inhibition or suppression of B1 cell activity in the host. Thus, an effective amount of IL-12 is an amount such that when administered to a host, it results in significant suppression of B1 cell activity relative to the B1 cell activity when an effective amount of IL-12 is not administered to a host. The suppression of B1 cell activity can be due to a decreased number of B1 cells that respond and/or due to diminished activity of B1 cells. In the method of treating a B1 cell disorder, an effective therapeutic amount of IL-12 is administered to the host, which is an amount that suppresses a significant amount of B1 cell activity in the host and results in the improved condition of the host (i.e., the B1 cell disorder is eliminated or diminished). The amount of IL-12 used to treat a B1 cell disorder in a host will vary depending on a variety of factors, including the size, age, body weight, general health, sex and diet of the host, and the time of administration, duration or particular qualities of the B1 cell disease state. Adjustment and manipulation of established dosage ranges are well within the ability of those skilled in the art.

In the experiments described herein, the influence of in vivo IL-12 treatment on B1 cells in BALB/c mice was examined. In normal mice, B1 cells are found in large percentages early in ontogeny and then as the animal ages, their representation decreases as B2 cells infiltrate the various lymphoid organs. By adulthood, B1 cells are rare in spleen (about 2% of total B cells in BALB/c spleens), lymph nodes, and peripheral blood. However, they remain present in large numbers in the peritoneal and pleural cavities where they exist as $CD5^{\pm}$ $CD23^-$ $MAC-1^+$ cells (Herzenberg, L. A., et al., Immunol. Rev., 93:81–102 (1986); Kipps, T. J., *Adv. Immunol.* 47:117–186 (1989); Hayakawa, K., et al., *Ann. Rev. Immunol.*, 6:197–218 (1988); Kasaian, M. T., et al., *Proc. Soc. Exp. Biol. Med.*, 197:226–241 (1991); Marcos, M. A. R., et al., *Eur. J. Immunol.*, 19:2031–2035 (1989)).

As described in Example 1, the potential influence of IL-12 on B1 cells was investigated by first examining the effects of in vivo administration of IL-12 on antibody responses to the phosphorylcholine (PC) hapten conjugated to keyhole limpet hemocyanin (PC-KLH) in mice. PC induces production of IgM, IgG1, IgG2a, IgG2b, IgG3, and IgA antibodies, offering the opportunity to examine the influence of IL-12 on expression of various isotypes. The results demonstrated that administration of IL-12 affected the immune response to PC-KLH by altering antibody isotype distribution and stimulating production of IFNγ.

Figure 4A:
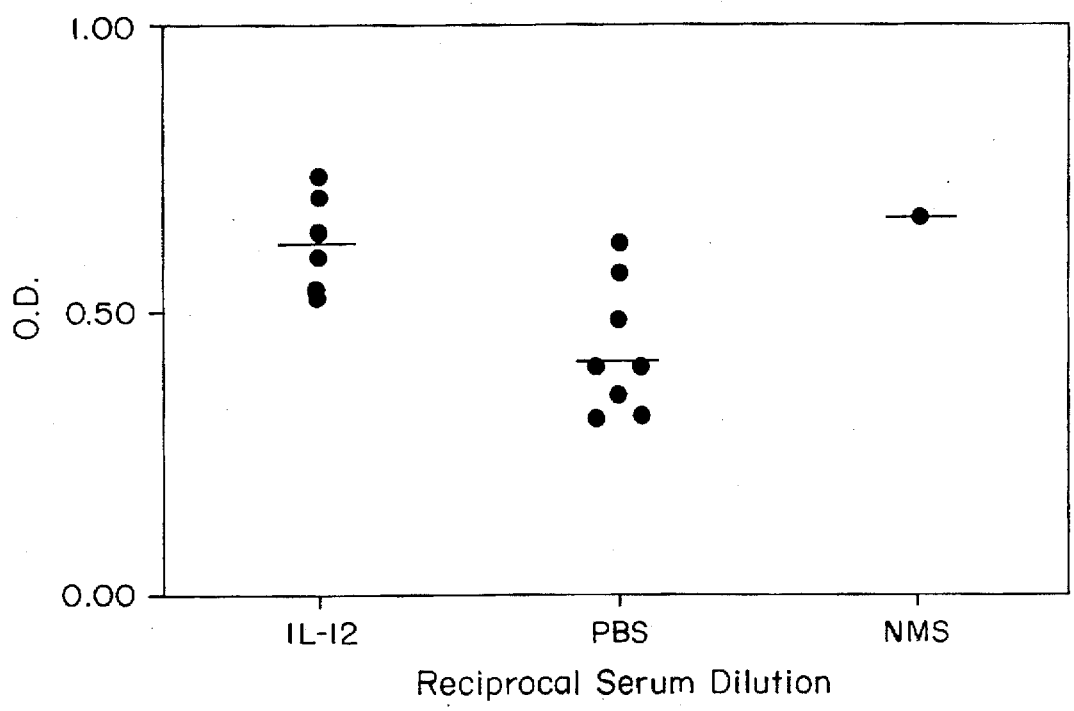
FIG. 4A is a graph showing the T15 idiotype production as measured by inhibition of TEPC 15 myeloma protein binding to anti-T15 idiotype.

The anti-PC response of BALB/c mice is dominated by antibodies that bear the T15 idiotype, which are secreted solely by B1 cells (Masmoudi, H., et al., Int. *Immunol.*, 2:515–520 (1990)). As described in Example 2, T15 idiotype levels in the sera of the treated animals were measured by inhibition ELISA in which dilutions of serum were tested for the ability to compete with TEPC 15 myeloma protein for binding to an anti-T15 idiotype mAb. It was found that sera from mice immunized with PC and treated with injection vehicle contained substantial T15 idiotype activity while sera from immunized and IL-12 treated mice contained levels of T15 idiotype similar to those seen in normal mouse serum (NMS), indicating suppression of B1 cell activity (FIG. 4A).

As described in Example 2, on day 7, the mice showed a typical Th2→Th1 shift, with higher levels of IgG2a anti-PC antibodies and lower levels of IgG1 antibodies as compared to control mice injected only with PBS. By day 17, both IgG1 and IgG2a antibody levels were enhanced in IL-12-treated mice. With regard to expression of other isotypes, day 7 IgM and possibly IgG3 were suppressed in IL-12-treated mice, while the levels of IgG2b and IgA were too low to measure with confidence at this time point (although one mouse did exhibit a strong IgA response after IL-12 injection). Total anti-PC antibody levels on day 7 were comparable between the two groups, but were increased on day 17 in cytokine-treated mice as compared to control animals.

Example 3 describes the flow cytometric analyses which demonstrated that IL-12 treatment caused a loss of peritoneal, but not splenic, B lymphocytes (FIG. 5). Small numbers of B2 cells, but not B1 cells, began to reappear in the peritoneum only after day 30.

IL-12 inhibited proliferation of B1 cells induced by IL-5 in vitro, as shown in Example 4 and shown in FIG. 6. The results show that IL-12 inhibits the functional activity of murine peritoneal B1 cells and that IL-12 would be a useful treatment for disease conditions that involve the B1 cell subset. Further experiments described in Example 4 showed that inhibition of B1 cells by IL-12 was not reversed by anti-IFN-γ antibody treatment.

Figure 7A:
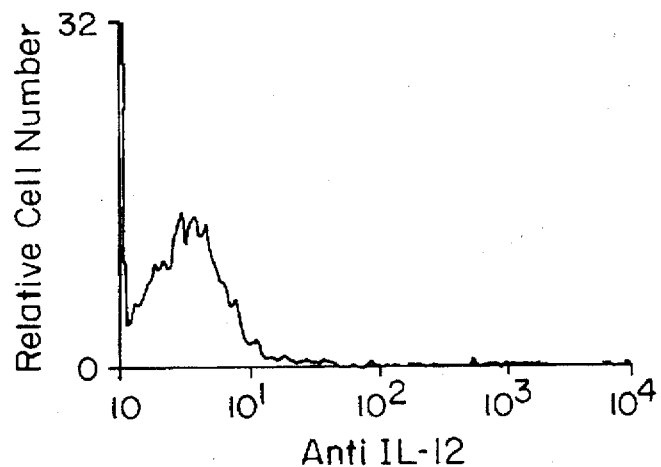
FIGS. 7A–7F are graphs of the fluorescence intensity versus relative cell number and demonstrate the in vivo expression of IL-12 receptor on murine B lymphocytes.
Figure 7B:
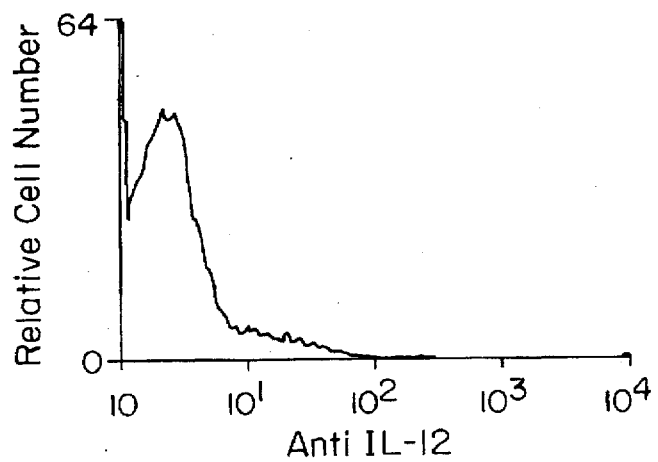
Figure 7C:
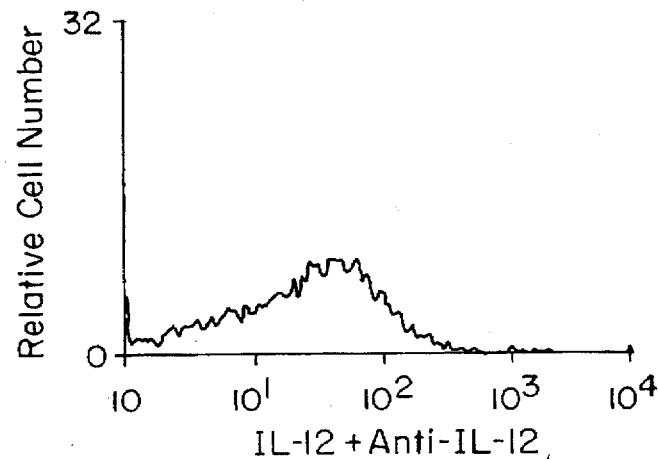
Figure 7D:
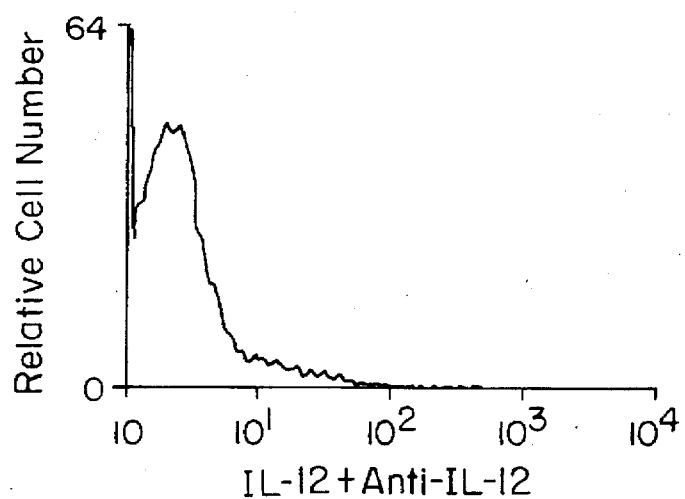
Figure 7E:
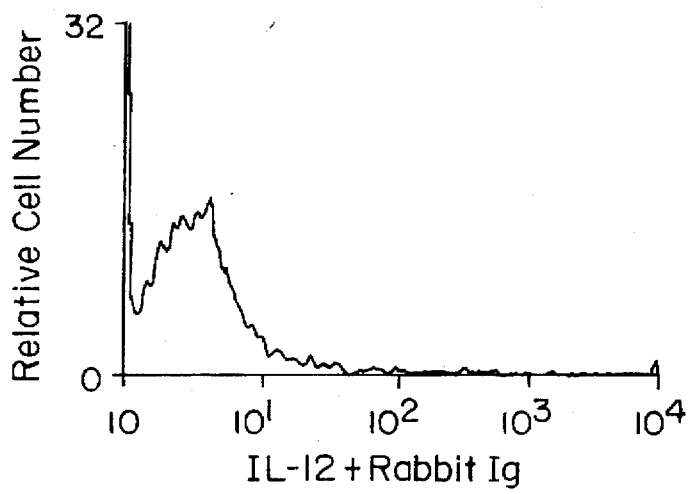
Figure 7F:
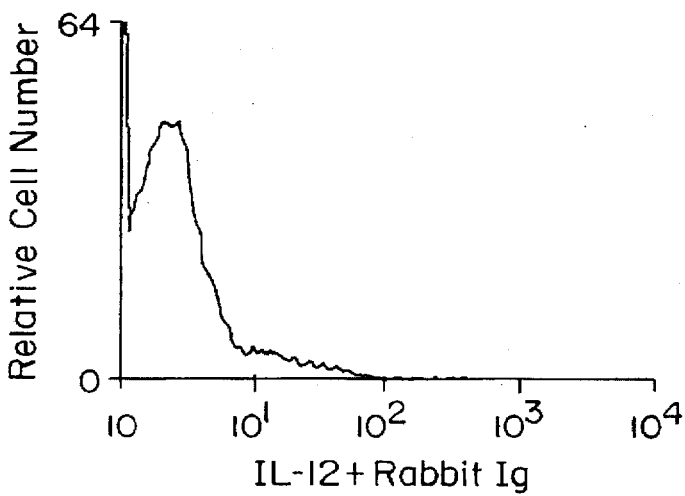
Figure 8A:
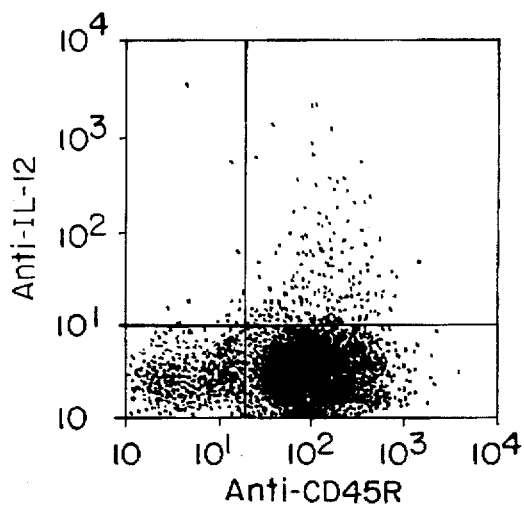
FIGS. 8A–8K are graphs of the fluorescence intensity versus relative cell number and demonstrate the subsets of PeC exhibiting binding of IL-12.
Figure 8B:
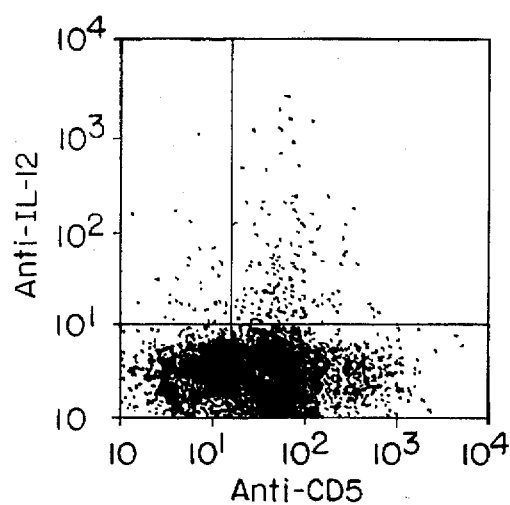
Figure 8C:
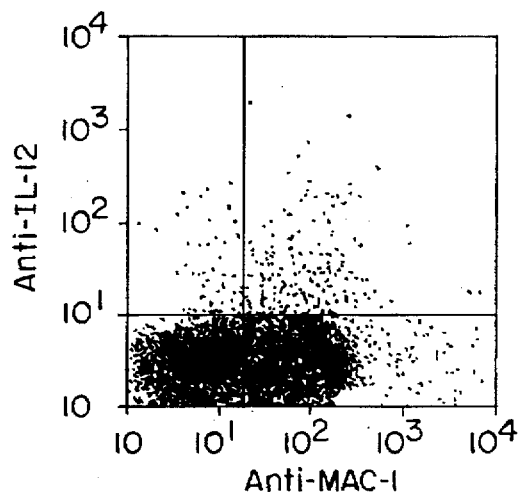
Figure 8D:
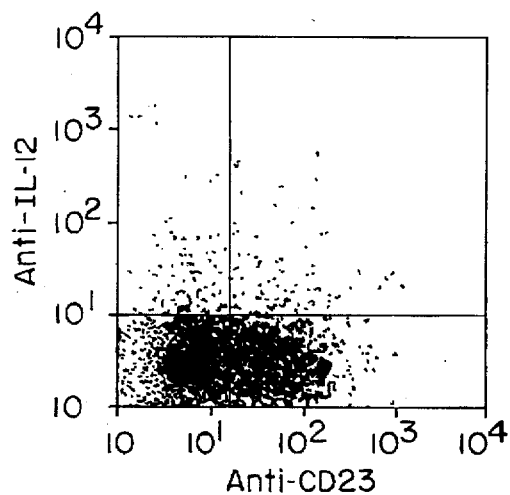
Figure 8E:
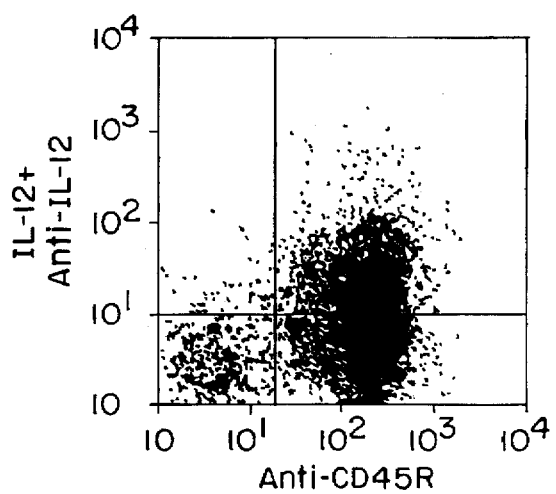
Figure 8F:
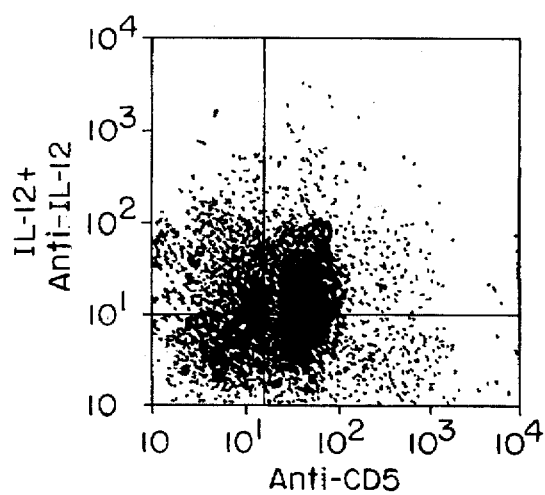
Figure 8G:
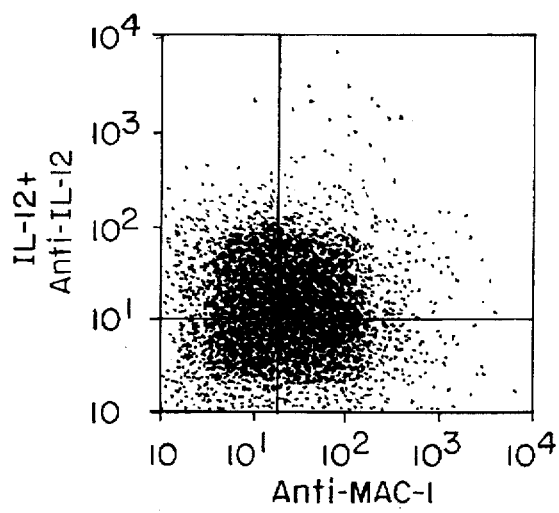

The possibility that IL-12 directly interacts with murine B cells was also investigated. Experiments by others in humans have thus far demonstrated an IL-12 receptor only on activated T and NK cells, but B1 cells were not examined (Desai, B. B., et al., *J. Immunol.*, 148:3125–3132 (1992)). Nothing is known about the mouse IL-12 receptor. As described in Example 5, to detect an IL-12 receptor on murine B cells, a three step staining method was employed: incubation with IL-12 followed by biotinylated rabbit anti-mouse IL-12, and streptavidin conjugated to allophycocyanin. Flow cytometric analysis revealed staining of lipopolysaccharide (LPS)-activated splenic B cells and fresh peritoneal B cells, but no staining of resting splenic B or T cells (FIG. 7). Positively stained peritoneal cells included both B1 cells [$CD45R(B220)^+CD23^-MAC-1^+$] and B2 cells [$CD45R(B220)^+CD23^+MAC-1^-$]. In addition, splenic B cell blasts obtained by LPS stimulation showed evidence for expression of the IL-12 receptor (FIG. 8C). All of the $IL-12R^+$ cells were B cells as judged by staining for IgM and CD45R(B220). In addition, the presence of IL-12 receptor on LPS-stimulated splenic B cells correlated with expression of the early activation marker, CD69 (FIG. 8E). Staining was ablated by omitting IL-12 from the procedure (FIG. 7A, 8C), showing that merely the presence of endogenous B cell IL-12 was not being detected. Staining was also lost by the use of biotinylated normal rabbit Ig instead of anti-IL-12 (FIG. 7E), or by the use of human IL-12 instead of murine IL-12. Murine IL-5 or IL-6 did not interfere with staining.

While proliferation of peritoneal cells in response to IL-5 was suppressed by IL-12, responsiveness of splenic B cells to LPS stimulation was not inhibited. However, exposure of splenic B cells to anti-IL-12 antibody, in the absence of added IL-12, caused four-fold inhibition of LPS activation.

None of the observed effects of IL-12 or anti-IL-12 on B cell activity were reversed by anti-IFNγ antibody. Taken together, the results show that murine B cells bear an IL-12 receptor and that while IL-12 suppresses the function of peritoneal B cell function, it is required for optimal activation of splenic B cells. That is, IL-12 suppresses the function of B1, but not B2, cells. These findings were surprising given the previously published results on human cells and indicate either that mice and humans differ dramatically in expression of the IL-12 receptor or that the homologous IL-12R-bearing human B cell population has not yet been identified.

The invention is further illustrated in the following examples.

EXEMPLIFICATION

Example 1

Influence of IL-12 on the murine antibody response to PC

In order to examine the effects of IL-12 on immune responses of B1 cells, mice were immunized with the antigen, phosphorylcholine-keyhole limpet hemocyanin (PC-KLH), which elicits antibody production by B1 cells (Masmoudi, H., *Int. Immunol.* 2:515 (1994)). BALB/c mice, purchased from Charles River Laboratories (Wilmington, Mass.) or the National Cancer Institute (Frederick, Md.), were used in the experiments. All mice used were at least 18 g.

Antigens and Immunizations

Phosphorylcholine (PC) was conjugated to bovine serum albumin (BSA) (FisherBiotech, Fair Lawn, N.Y.) and keyhole limpet hemocyanin (KLH) as described (Wu, P. and Ward, R. E., *Cell. Immunol.* 155:345 (1994); Chesebro, B. and Metzger, H., *Biochemistry* 11:766 (1972)). Briefly, 35 mg of p-aminophenyl phosphorylcholine (Sigma) in 1.6 ml $dH_2O$ were mixed with 0.6 ml of 1M $NaNO_2$ and 0.2 ml of 4N HCl. The pH was adjusted with 1N NaOH to 9.0 and the mixture was incubated at 0° C. for 1 hr. BSA or KLH at a concentration of 100 mg in 5.0 ml of 0.1M sodium borate buffer, pH 9.2, was then added. After overnight incubation, the mixtures were dialyzed against 3 changes of 2 liters of phosphate buffered saline (PBS), pH 7.4.

Recombinant murine IL-12, generously provided by Dr. Brian Hubbard, Genetics Institute (Cambridge, Mass.), was purified as described (Gately, M. K., et al., *Int. Immunol.* 6:157 (1994). Murine rIL-12 was >96% pure by SDS-Page analysis and contained <1.2 U/mg of endotoxin activity (by Limulus amebocyte assay). Its specific activity was $4.9 \times 10^6$ U/mg as determined by a phytohemagglutinin (PHA) proliferation assay. Mice were injected intraperitoneally with 1 µg rIL-12 in PBS-1% normal mouse serum consecutively for 3 or 5 days. Control mice received PBS-1% normal mouse serum only. No difference was observed between mice treated for 3 days or 5 days. Animals received intraperitoneal injections of 100 µl of PC-KLH diluted 1:10 in PBS then emulsified in Freund's complete adjuvant (Gibco BRL, Grand Island, N.Y.) on the middle day of treatment (day 0).

Antibodies

Goat anti-mouse IgG1, IgG2a, IgM, IgG2b, and IgG3 mAbs conjugated to alkaline phosphatase were obtained from Southern Biotechnology Associates, Inc. (Birmingham, Ala.).

For purification of mAb, the cells were grown for 2 weeks in RPMI 1640–10% (v/v) fetal calf serum (Irvine Scientific, Santa Ana, Calif. and Hyclone Laboratories, Inc., Logan, Utah). Supernatants were dialyzed against saturated ammonium sulfate (100 ml supernatant to 1 liter of ammonium sulfate) for 3 days at 4° C. to precipitate proteins. The precipitates were dialyzed against phosphate buffered saline (PBS) overnight and passed over a Sepharose 6B column (Sigma) containing protein G (kindly provided by Dr. Michael Boyle, Medical College of Ohio, Toledo, Ohio). Antibody was eluted using 0.2M glycine sulfate, pH 2.3, dialyzed against PBS, and concentrated using a Centriprep-10 concentrator (Amicon, Beverly, Mass.). Absorbance at 280 nm was used to determine antibody concentrations.

ELISAS

Sera were tested for anti-PC antibodies by coating microtiter plates (Corning Costar Corp., Cambridge, Mass.) with PC-BSA diluted 1:1000 in PBS overnight at 4° C. The coating solution was removed and the plates were washed 3 times with PBS containing 0.1% (w/v) gelatin and 0.05% (v/v) Tween 20. The plates were incubated with two-fold dilutions of sera for 2 hr at room temperature. After washing, detecting antibody was added, followed by streptavidin-alkaline phosphatase (Bio-Rad Laboratories, Hercules, Calif.). Substrate, p-nitrophenyl phosphate (Sigma), was added and the absorbance at 405 nm was determined using a Bio-Tek plate reader (Bio-Tek Instruments, Inc., Winooski, Vt.).

Results

Mice received phosphate buffered saline (PBS) or 1 µg IL-12 in 1% normal mouse serum on days −1, 0, 1 and PC-KLH on day 0. Sera were tested by ELISA at day 7 (FIG. 1A and 1C; FIG. 2A, 2C, 2E and 2G) and day 17 (FIG. 1B and 1D; FIG. 2B, 2D, 2F and 2H).

Figure 1B:
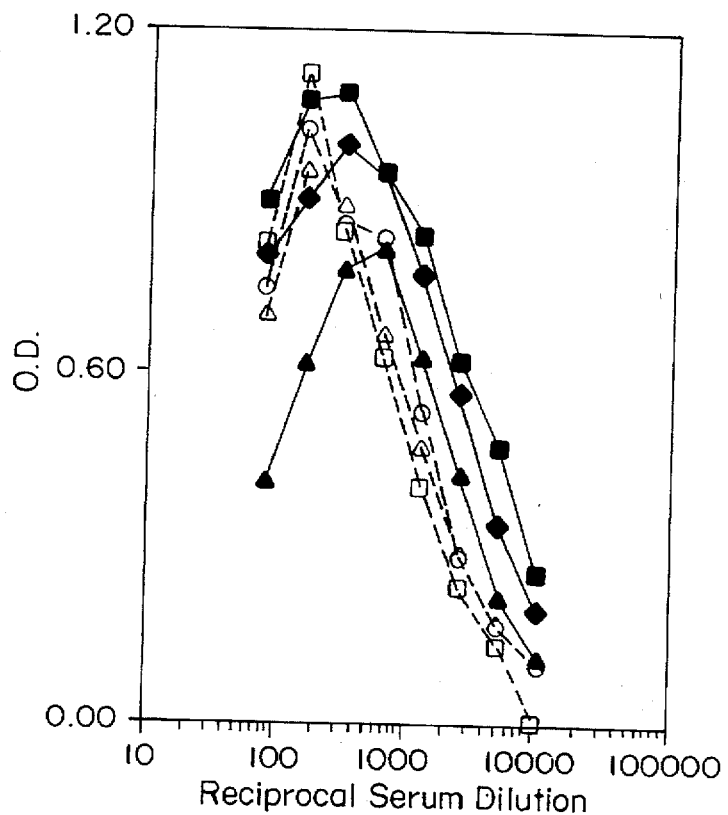
Figure 1C:
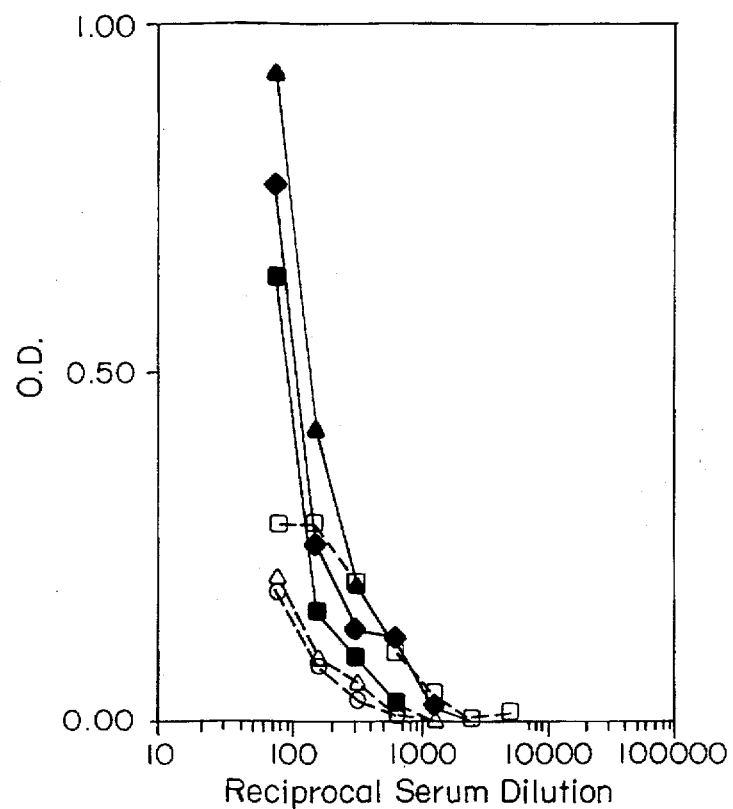
Figure 1D:
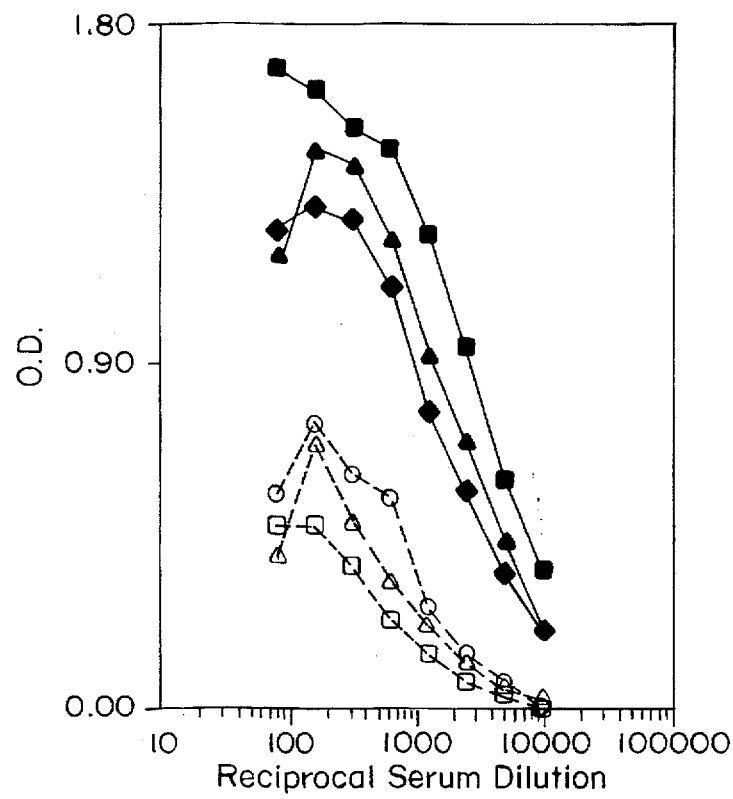
Figure 2A:
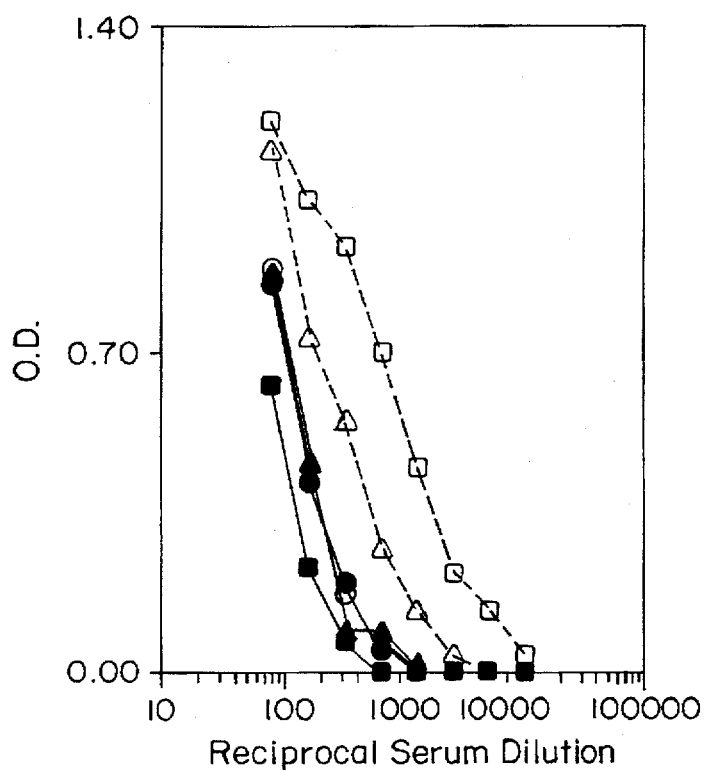
FIGS. 2A–2H are graphs of the reciprocal serum dilution versus optical density at 405 nm demonstrating the effects of IL-12 on anti-PC antibody production (solid Lines indicate mice receiving IL-12 and dashed lines indicate mice receiving PBS).
Figure 2B:
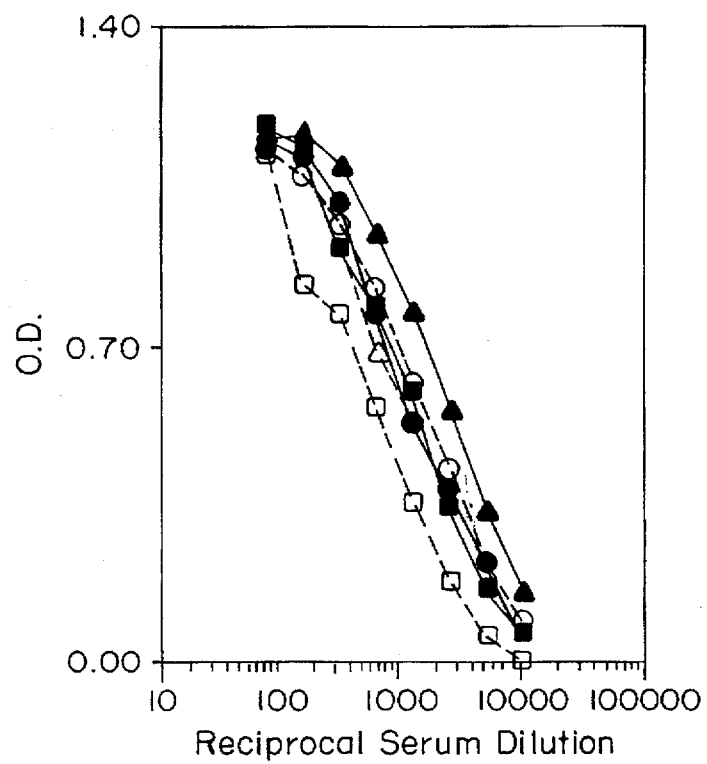
Figure 2C:
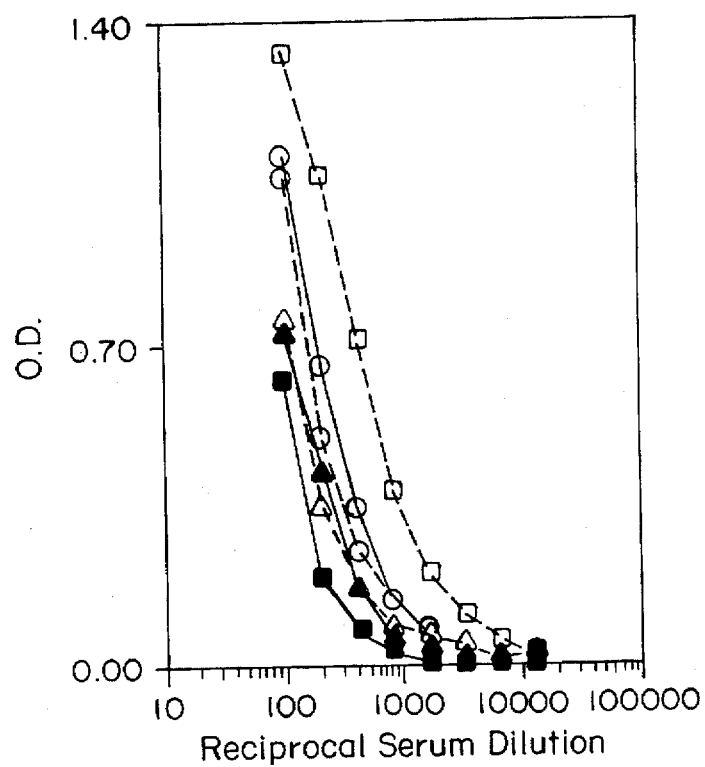
Figure 2D:
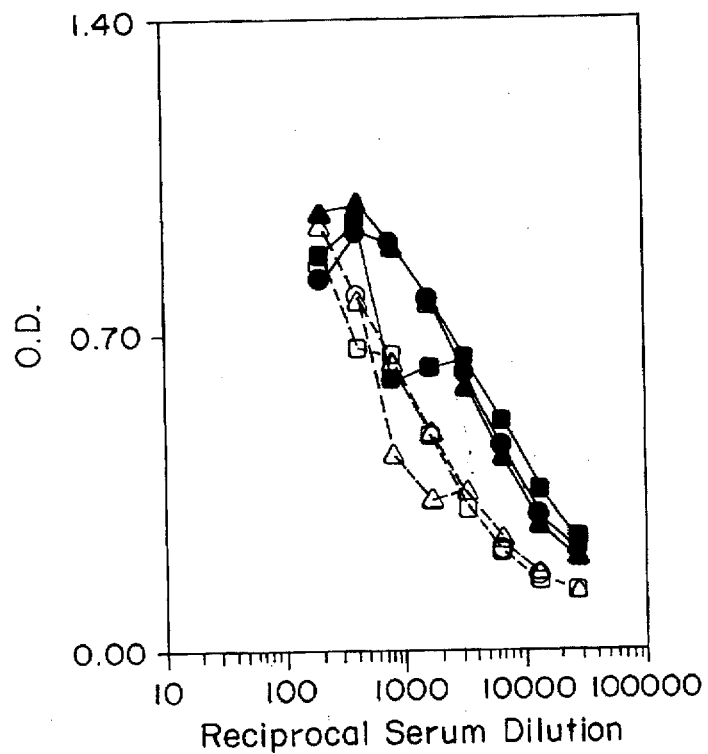
Figure 2E:
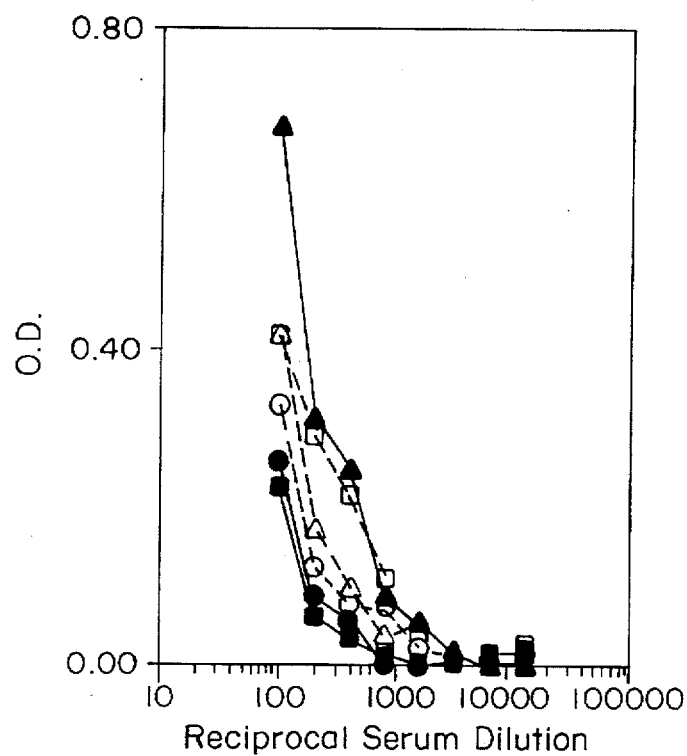
Figure 2F:
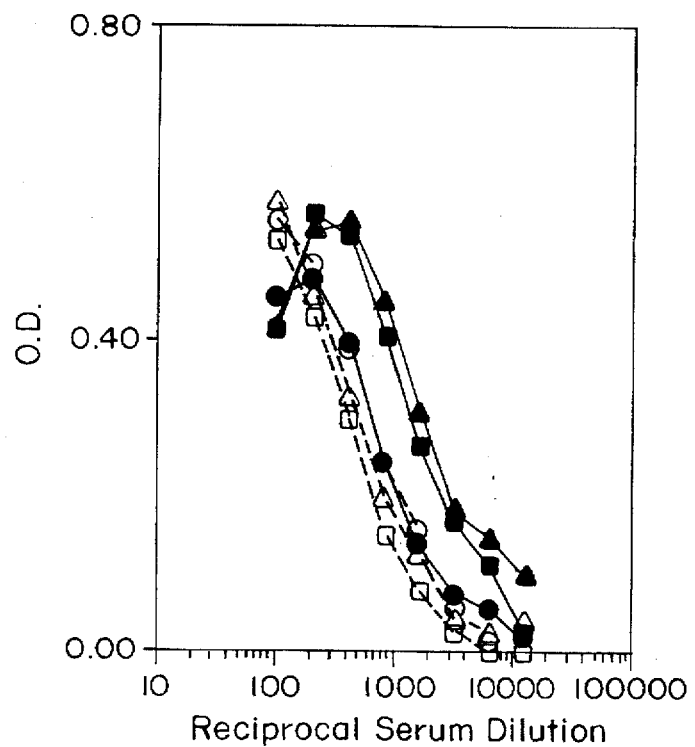
Figure 2G:
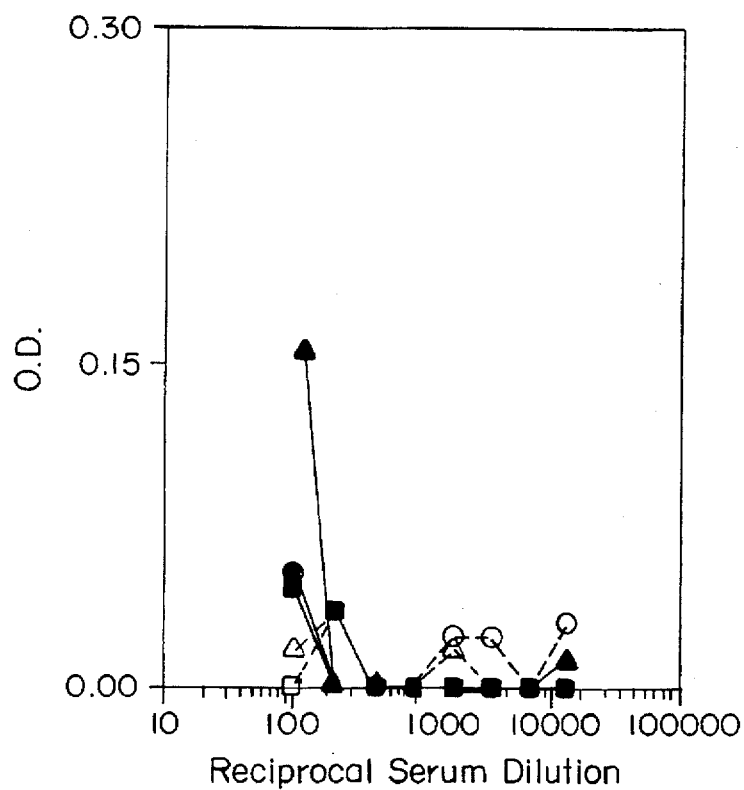
Figure 2H:
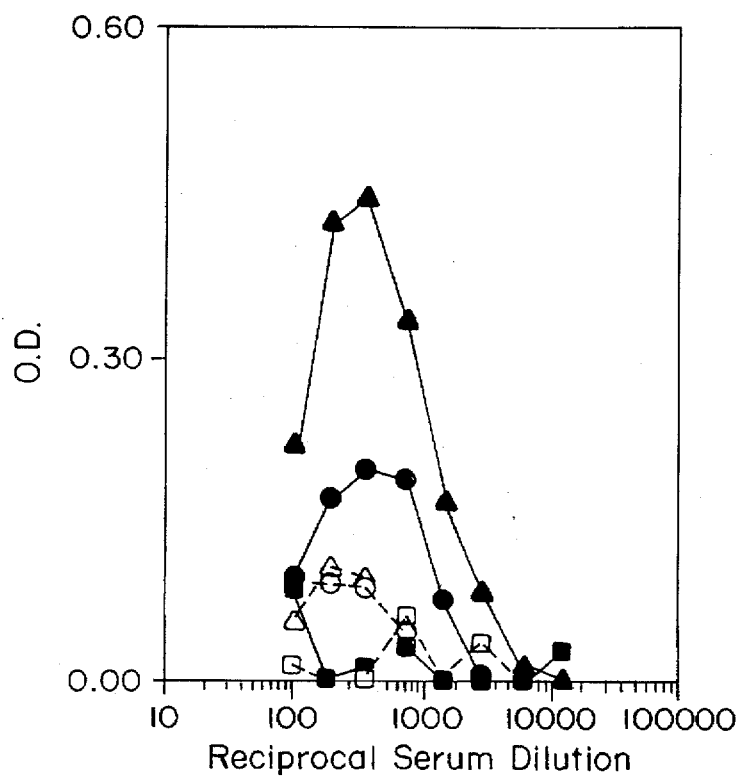

IgG1 anti-PC responses are shown in FIG. 1A and FIG. 1B; IgG2a anti-PC responses are shown in FIG. 1C and 1D. IgM anti-PC responses are shown in FIG. 2A and 2B, IgG3 anti-PC responses are shown in FIG. 2C and 2D, IgA anti-PC responses are shown in FIG. 2E and 2F, and IgG2b anti-PC responses are shown in FIG. 2G and 2H.

Mice that received 1 µg of recombinant murine IL-12 for three consecutive days produced less IgG1 anti-PC at day 7 than control treated mice (FIG. 1A). By day 17, however, the IL-12 treated mice had titers of IgG1 anti-PC greater than control mice (FIG. 1B). Enhanced IgG2a anti-PC production was observed at both 7 days and 17 days post-immunization (FIG. 1C and D). There also appeared to be a slight suppression of IgM antibodies at day 7 in mice receiving IL-12 (FIG. 2A), but this suppression disappeared by day 17 (FIG. 2B). Levels of IgG3 and IgA anti-PC antibodies were similar to controls at day 7 (FIG. 2C and E), but were up to ten-fold greater in treated mice at day 17 (FIG. 2 and F). Very little IgG2b was produced at either timepoint (FIG. 2G and H).

IFN levels

In addition to its effects on isotype production, IL-12 is a potent inducer of IFNγ (Chan, S. H., et al., *J. Exp. Med.* 173:869 (1991); D'Andrea, A., et al., *J. Exp. Med.* 176:1387 (1992); Tripp, C. S., et al., *Proc. Natl. Acad. Sci. USA* 90:3725 (1993)). To examine the levels of IFNγ in PC-KLH immunized mice, mice were treated as described above. Periaortic lymph nodes were removed at day 5 and the cells were cultured in the presence of media, KLH, or Ribonuclease A (Sigma) (RNase) for three days. RNase and KLH were added at 100 µg/ml. Supernatants were tested by ELISA for IFNγ and concentrations were determined by comparison to a standard curve.

XMG1.2 anti-IFNγ mAb was purified from ascites fluid produced in SCID mice and passed over a protein A (Repligen, Cambridge, Mass.) sepharose column. A Limulus amebocyte lysate kit (BioWhittaker, Walkersville, Md.) was used to determine that the purified Ab had <1 U/ml of endotoxin activity.

IFNγ was detected in culture supernatants as previously described (Yang, X. and HayGlass, K. T., *J. Immunoassay* 14:129 (1993)). Easy Wash microtiter plates (Corning Costar Corp.) were coated with 0.1 µg/well anti-IFNγ (R4-6A2) overnight at 4° C. R4-6A2 anti-IFNγ was obtained from ATCC (Spitalny, G. L. and E. A. Havell, *J. Exp. Med.* 159:1560 (1984). Plates were washed with PBS containing 0.05% Tween 20 and blocked with PBS containing 10% fetal calf serum (Hyclone) for 2 hr at room temperature. Culture supernatants (100 µl) were added and incubated at room temperature for 4 hr. After washing, biotinylated anti-IFNγ (XMG1.2) was added followed by horseradish-peroxidase coupled to streptavidin (Vector Laboratories, Burlingame, Calif.). ABTS substrate (Kirkegaard and Perry Laboratories, Gaithersburg, Md.) was added after washing. Concentrations of cytokine were determined by comparison to a standard curve.

Results

Figure 3:
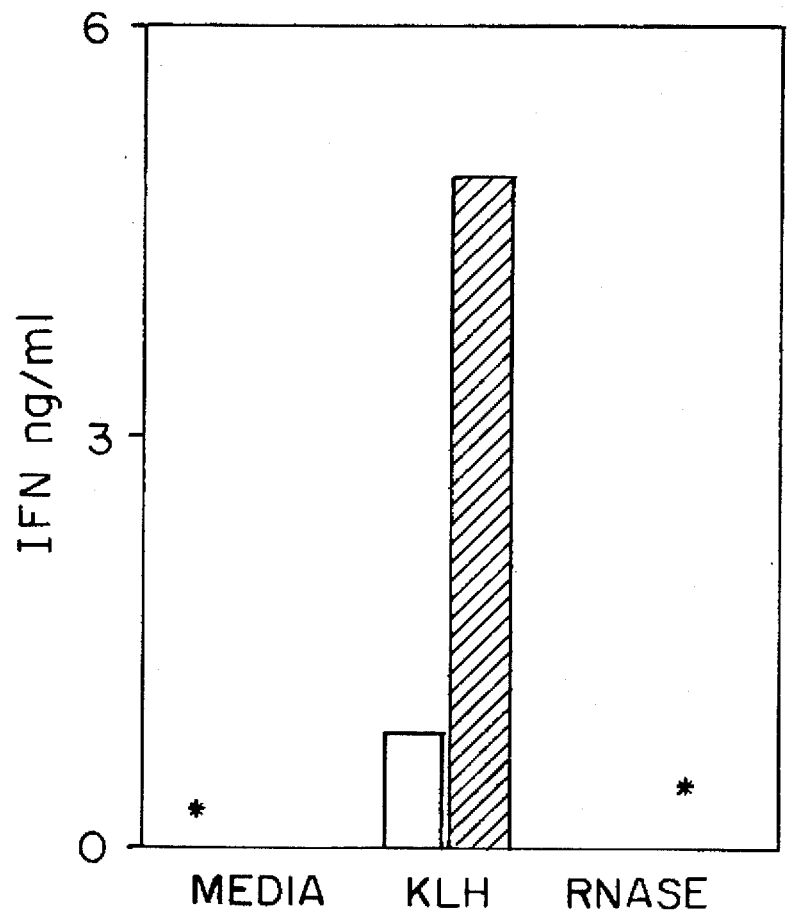
FIG. 3 is a bar graph illustrating the production of IFNγ by lymph node cells from IL-12 and PBS treated mice (a(*) indicates >0.001 ng/ml; empty box indicates mice receiving PBS and shaded box indicating mice receiving IL-12).

Supernatants of cells from both groups cultured with media or RNase contained very little IFNγ (FIG. 3). In contrast, addition of KLH caused lymph node cells from mice treated with IL-12 to produce significantly more IFNγ than PBS treated mice. These results indicate that IL-12 is indeed affecting the immune response to PC-KLH by altering antibody isotype distribution and stimulating production of IFNγ.

Example 2

Suppression of T15 idiotype production by in vivo administration of IL-12

In BALB/c mice, anti-PC antibodies bearing the T15 idiotype dominate the anti-PC response and are secreted solely by B1 cells (Masmoudi, H., *Int. Immunol.* 2:515 (1994)). Thus, measure of serum T15 idiotype in immunized mice is a convenient indication of B1 cell activity. T15 idiotype was measured by the ability of serum to inhibit TEPC 15 myeloma protein binding to the anti-T15 idiotype mAb, AB1-2. The AB1-2 anti-T15 idiotype cell line was obtained from ATCC (Kearney, J. F., et al., *Eur. J. Immunol.* 11:877 (1981)). Mice were treated as described in Example 1. Sera were tested on day 7 by ELISA.

Antibodies

Anti-mouse IgA coupled to biotin, TEPC 15 myeloma protein, and alkaline-phosphatase-conjugated anti-mouse IgG whole molecule were purchased from Sigma (St. Louis, Mo.).

ELISA

The ELISA protocol described in Example 1 was modified slightly to detect T15 idiotype. Microtiter plates were coated with 0.1 µg/well AB1-2 in PBS and incubated overnight at 4° C. After washing, plates were incubated with 0.01 µg/well of TEPC 15 together with 50 µg/well of serum as inhibitor. Binding of TEPC 15 was detected with anti-IgA-biotin and streptavidin-alkaline phosphatase.

Results

Figure 4B:
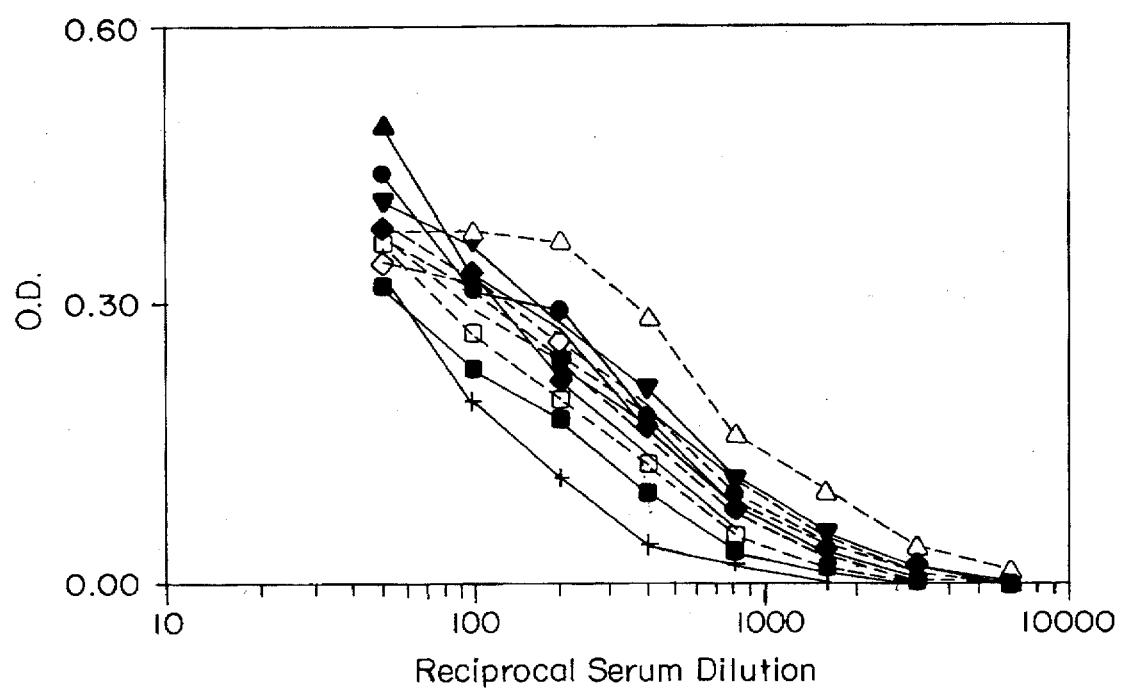
FIG. 4B is a graph of reciprocal serum dilution versus OD at 465 nm demonstrating that IL-12 causes reduction in serum antibodies bearing the T15 idiotype (solid lines indicate mice receiving IL-12 and dashed lines indicate mice received PBS).

FIG. 4A shows T15 idiotype production as measured by inhibition of TEPC 15 binding to anti-T15 idiotype (AB1-2). Each point represents an individual mouse tested at a 1:50 serum dilution (6 IL-12 mice and 8 PBS mice). FIG. 4B shows total anti-PC antibodies in serum which were measured as described.

Sera from mice that received IL-12 showed significantly less inhibition (with a p value <0.01 according to Student's t-test) than sera from PBS-treated mice (FIG. 4A), indicating that IL-12 suppressed serum T15 idiotype expression. This decrease was observed despite similar levels of total anti-PC antibodies in both groups of mice (FIG. 4B). By day 17, all mice had similar levels of T15 idiotype (data now shown). These data indicate that IL-12 inhibits B1 cell activity as reflected in decreased production of serum antibody.

Example 3

Effects of IL-12 on levels of peritoneal B cells

In mice, a large population of B1 cells is found in the peritoneal cavity. In order to determine the effects of intraperitoneal administration of IL-12 on peritoneal cells, flow cytometric analysis was performed on PeC obtained from mice immunized with PC-KLH in Complete Freund's Adjuvant (CFA) at 5, 7, 17, and 30 days post-immunization. Mice received PBS or IL-12 for 5 days (−2, −1, 0, 1, 2) and PC-KLH on day 0.

Cell cultures

PeC or periaortic lymph node cell were cultured in 96 well microtiter plates ($2\times10^5$ cells/well) in RPMI 1640 containing 10% FCS.

Antibodies

The B3B4 anti-CD23 (Rao, M., et al., *J. Immunol.*, 138:1845 (1987)) and RA3-6B2.1 anti-CD45R (B220) (Coffman, R. L., et al., *Nature*, 289:681 (1981) cell lines were kindly supplied by Drs. Daniel H. Conrad (Medical College of Virginia, Virginia Commonwealth University, Richmond, Va.) and Robert L. Coffman (DNAX, Palo Alto, Calif.), respectively. The 2.4G2 anti-FcγII (Unkeless, J., *J. Exp. Med.*, 150:580 (1979)), anti-CD5 53-7.313 (Ledbetter, J. A., et al., *Immunol. Rev.*, 47:63 (1979), anti-CD3 145-2C11 (Leo, O. M., et al., *Proc. Natl. Acad. Sci., USA*, 84:1374 (1987) and M1/70.15.11.5HL anti-MAC-1 hybridoma cell lines (Springer, T., et al., *Eur. J. Immunol.*, 8:539 (1978) were obtained from ATCC (Rockville, Md.). Anti-mouse IgM conjugated to FITC was obtained from Zymed (San Francisco, Calif.). Anti-CD3 and anti-CD69 conjugated to FITC, and anti-IgD conjugated to PE were purchased from PharMingen (San Diego, Calif.). The mAbs were purified as described in Example 1.

For coupling anti-B220 to fluorescein isothiocyanate (FITC), antibody was dialyzed overnight at 4° C. against 0.05M borate buffered saline, pH 9.2. The mAb was then incubated with FITC (1 mg mAb with 100 µg FITC in dimethylsulfoxide) for 2 hr at room temperature. The mixture was passed over a PD-10 column to isolate the FITC conjugate.

For biotinylation of anti-MAC-1 and anti-CD23, 100–500 µg of protein in PBS were incubated overnight at 4° C. with a 1/10 volume of 20 mg/ml N-hydroxysuccinimidobiotin in dimethylsulfoxide (Sigma). The mixtures were then passed over PD-10 columns (Pharmacia, Piscataway, N.J.) and 0.5 ml fractions were collected. Fractions were tested by ELISA for activity and appropriate fractions were pooled. The conjugates were stored at 4° C. in 0.01% (w/v) sodium azide.

Anti-mouse Ly-1 conjugated to biotin and anti-mouse IgM conjugated to FITC were obtained from Becton-Dickinson Mountain View, Calif.) and Zymed (San Francisco, Calif.), respectively.

Flow cytometric analyses

Peritoneal cells (PeC) were obtained from mice by injection of 5–10 ml of Hanks' Balanced Salt Solution (HBSS) containing 0.1% gelatin. Single cell suspensions of spleen cells (SPC) were prepared by passage through wire mesh, and red blood cells were removed by Lympholyte M (Cedar Lane Laboratories, Limited, Ontario, Canada) density gradient centrifugation. Cells were incubated ($5 \times 10^5$ cells/sample) with 50 µl of 2.4G2 anti-FcγII supernatant to block Fc receptor binding for 15 min on ice. The 2.4G2 anti-FcγII cell line was obtained from ATCC (Rockland, Md.) (Unkeless, J. C., *J. Exp. Med.* 150:580 (1982). Cells were then incubated for 15 min with biotinylated Ab and washed with buffer, followed by a second Ab coupled to FITC together with streptavidin-allophycocyanin (Molecular Probes, Eugene, Oreg.). Analysis was performed on an EPICS ELITE flow cytometer (Coulter, Hialeah, Fla.) and lymphocytes were gated based on 90° and forward light scatter. Further analysis of listmode files was performed using the WinMDI version 1.3.4 software.

Figure 5A:
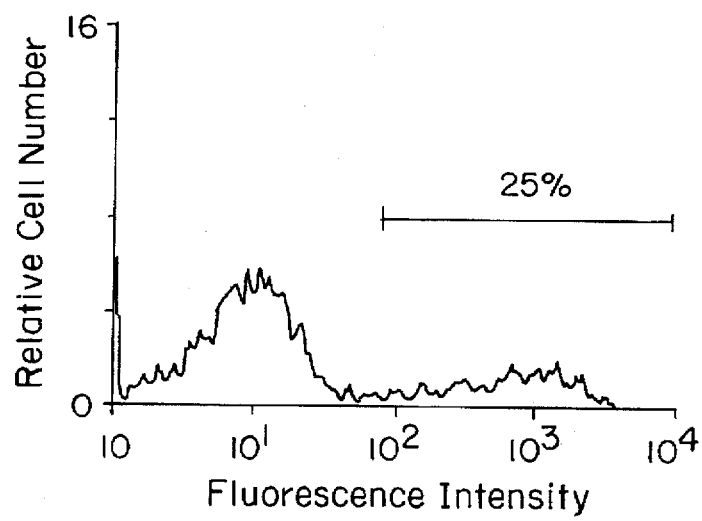
FIGS. 5A–5H are graphs of fluorescence intensity versus relative cell number which demonstrate the loss of peritoneal B lymphocytes by IL-12 treatment.
Figure 5B:
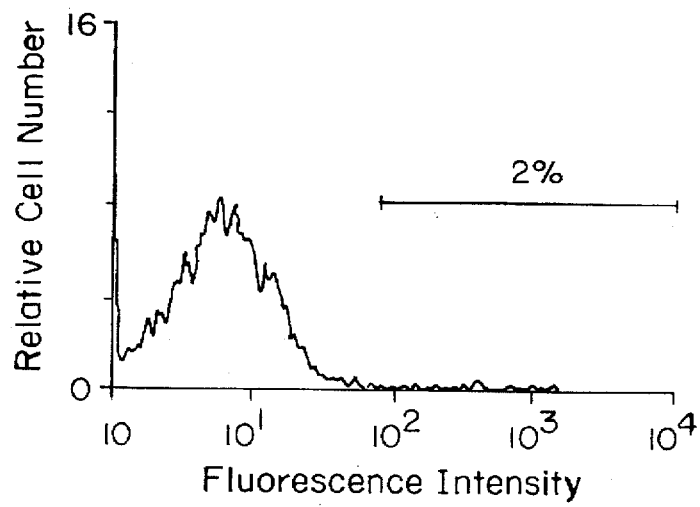
Figure 5C:
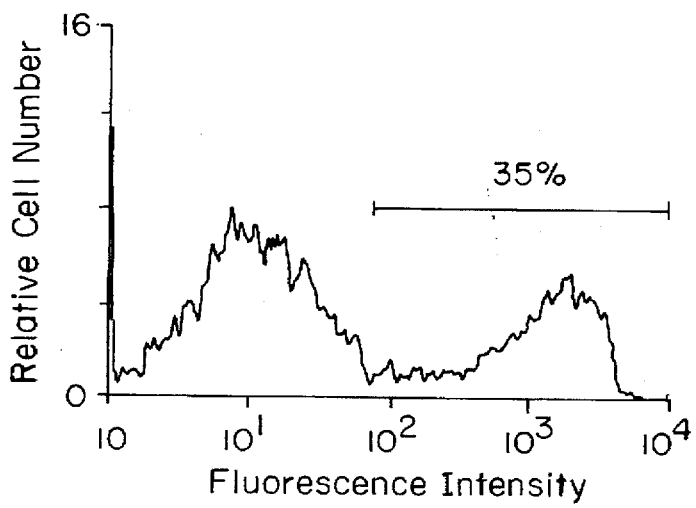
Figure 5D:
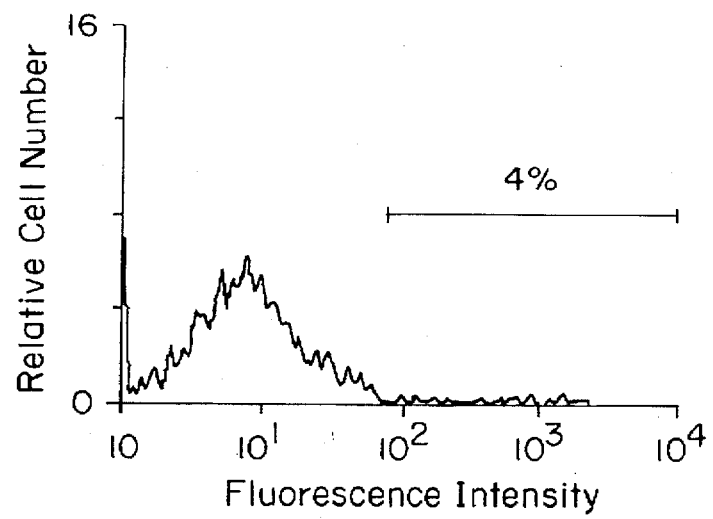
Figure 5E:
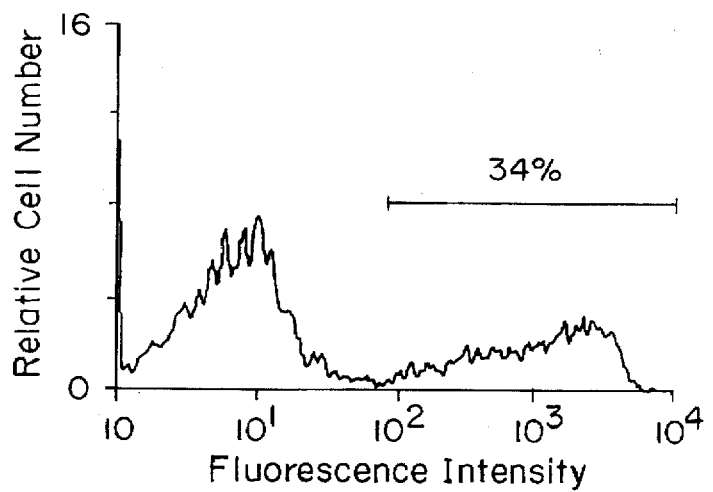
Figure 5F:
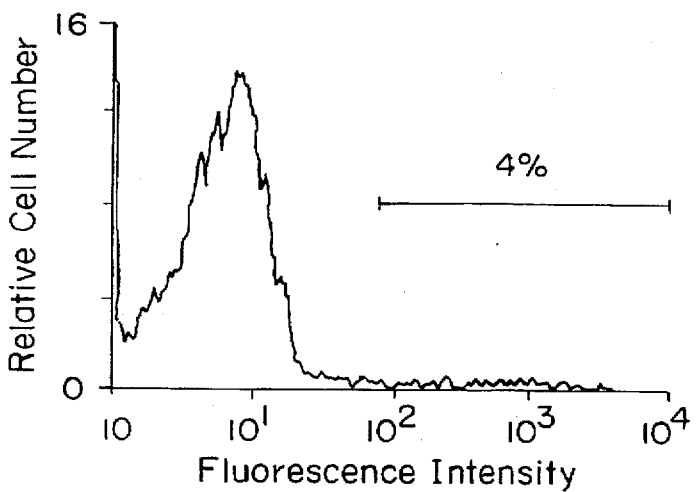
Figure 5G:
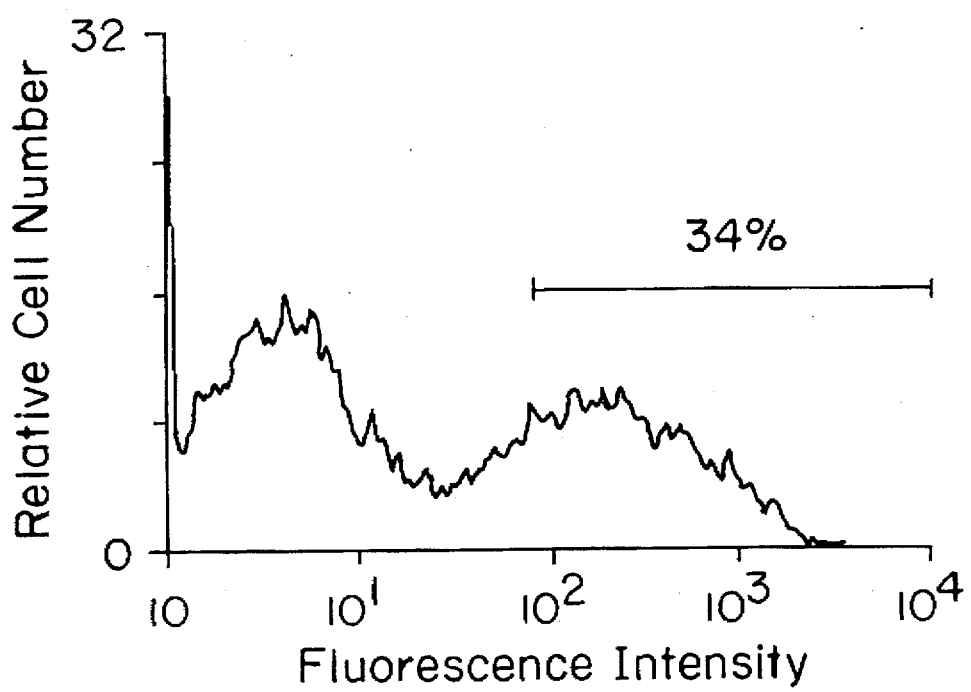
Figure 5H:
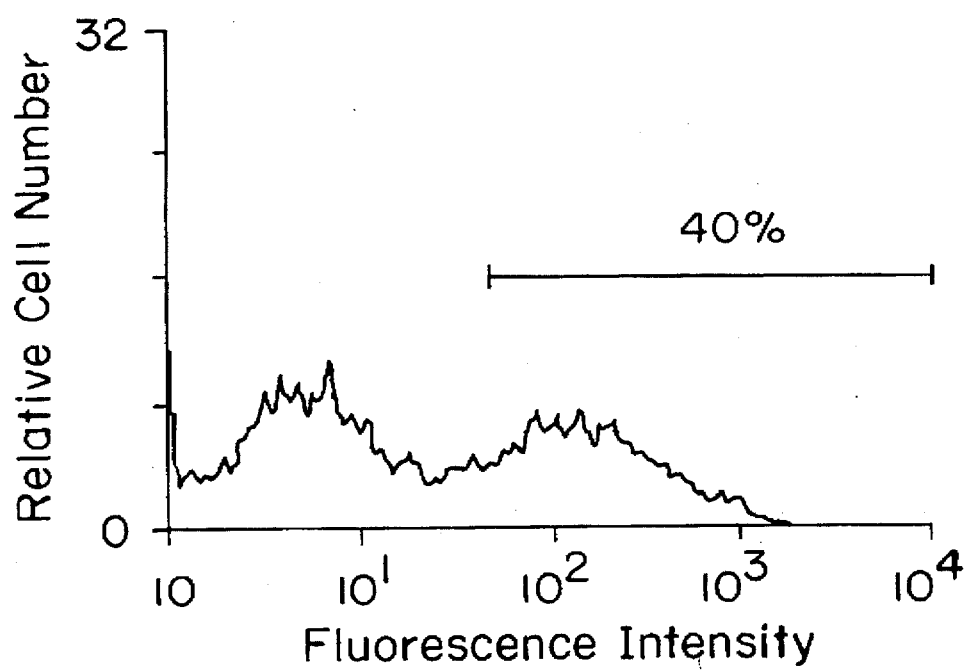

Peritoneal cells (FIG. 5A–5F) were pooled from two mice for each group and were stained with anti-IgM-FITC on day 5 (FIG. 5A and 5B), day 7 (FIG. 5C and 5D), and day 16 (FIG. 5E and 5F). Spleen cells pooled from two mouse per group were stained on day 7 (FIG. 5G and 5H). Mice received PBS (FIG. 5A, 5C, 5E, and 5G) or IL-12 (FIG. 5B, 5D, 5F, and 5H). Percentages of IgM-bearing lymphocytes are indicated.

Flow cytometric analyses revealed a striking loss of peritoneal B lymphocytes in IL-12-treated mice 5 days after treatment (FIG. 5A and 5B, Table). Peritoneal B1 and B2 lymphocytes were decreased about ten-fold at day 7 (FIG. 5C and 5D), while percentages of splenic B cells were similar between IL-12 and PBS treated mice (FIG. 5G and 5H). Surprisingly, the peritoneal B cells were still present in only very low numbers at day 17 (FIG. 5E and 5F) and only began to reappear at day 30 (38% IgM$^+$ cells in control mice versus 8% IgM$^+$ cells in IL-12 treated mice). At all time points, mice receiving IL-12 showed increased T lymphocytes in the peritoneal cavity (see Table). Numbers of T and B cells do not add up to total numbers of lymphocytes due to the presence of some macrophages (IgM$^-$ CD45R$^-$ CD5$^-$ MAC1$^+$ cells) in the lymphocyte gate.

Injection of CFA and IL-12 without PC-KLH also caused loss of peritoneal B cells, but administration of IL-12 alone had only slight effects (data not shown). These results demonstrate that a single course of IL-12 treatment profoundly suppressed levels of both B1 and B2 cells in the peritoneal cavity, causing their numbers to be drastically reduced. This effect, however, was not observed with injection of IL-12 alone, but required cell stimulation.

Example 4

Suppression of in vitro IL-5 induced proliferation of peritoneal B cells

To further examine the effects of IL-12 on B1 cells, peritoneal cells were cultured in vitro in the presence of IL-5. B1 cells express receptors for IL-5 and have been shown to proliferate in response to this cytokine (Wetzel, G. G., *Eur. J. Immunol.* 19:1701 (1989)); Hitoshi, Y., et al., *J. Immunol.* 144:4218 (1990)); Wetzel, G. D., Scan. *J. Immunol.* 31:91 (1990)).

Peritoneal cells were cultured with media, IL-5, IL-12 (50 ng/ml), or a mixture of IL-5 and various dilutions of IL-12 at a final concentration of 50, 5 or 0.5 ng/ml. Proliferation was measured after 72 hr by $^3$HTdR uptake. See FIG. 6A. In addition, peritoneal cells were cultured as described above and with media alone (shaded box), 50 µg/ml anti-IFNγ (empty box), or 50 µg/ml normal rat Ig (hatched). See FIG. 6B.

Recombinant murine IL-5 (Genzyme, Corp., Cambridge, Mass.) was added at a final concentration of 100 U/ml and IL-12 was used at a final concentration of 50, 5, or 0.5 ng/ml. For proliferation assays, 1 µCi of $^3$HTdR (ICN Radiochemicals, Irvine Calif.) was added after 48 hr and cells were harvested onto glass fiber filters after 72 hr. Bound radioactivity was determined using a Beckman LS 3801 scintillation counter. For cytokine production, supernatants were collected after 72 hr.

Results

Figure 6A:
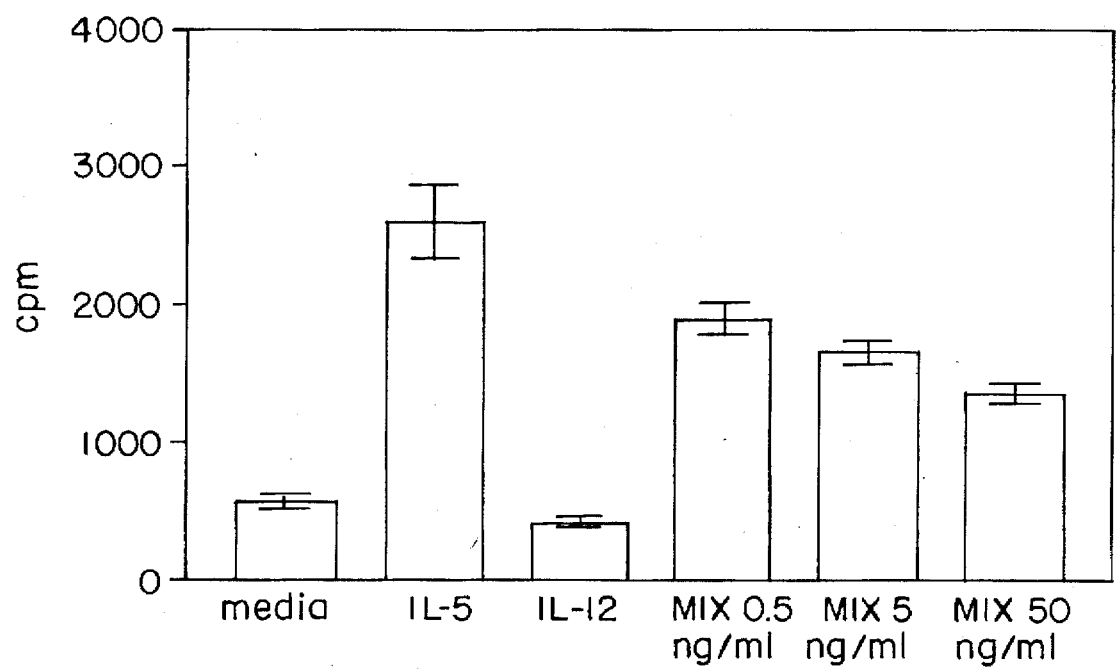
FIGS. 6A–6B are bar graphs illustrating the inhibition of IL-5-induced proliferation of peritoneal cells (PeC) in vitro (PeC were cultured with media alone (shaded box), 50 μg/ml anti-IFNγ (empty box) or 50 μg/ml normal rat Ig (hatched)).
Figure 6B:
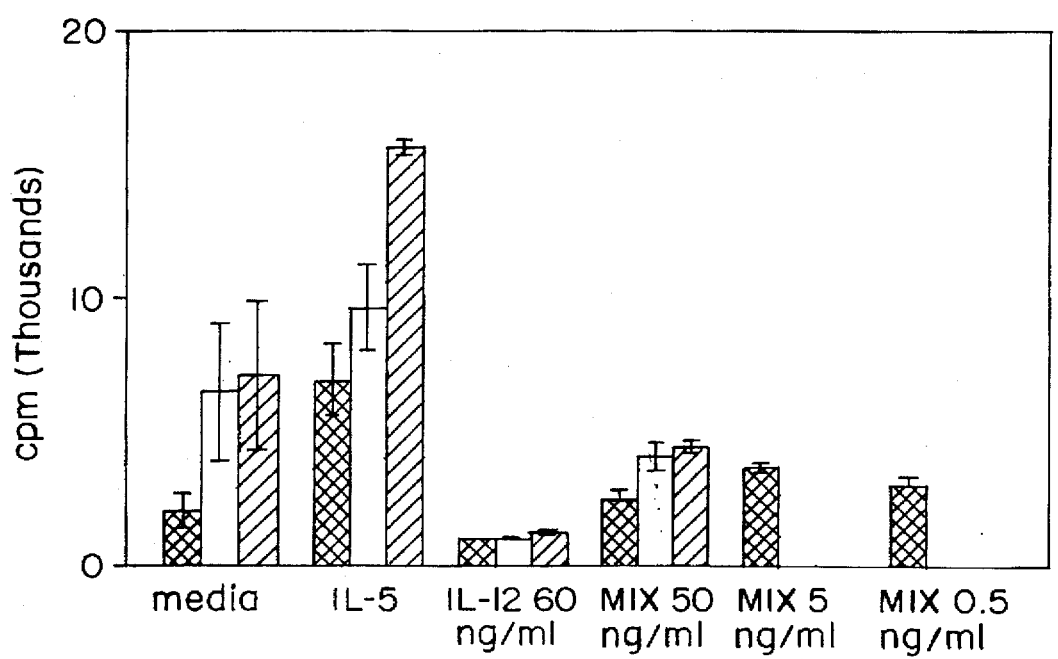

Addition of IL-12 caused inhibition of IL-5-induced proliferation in a dose-dependent manner (FIG. 6A). As IFNγ has previously been shown to inhibit IL-5 induced proliferation of B1 cells (Hitoshi, Int. *Immunol.* 1:185, 1989), IL-12 in these experiments may have been acting through IFNγ production. To examine this possibility, cells were cultured in media or in the presence of anti-IFNγ IFNγ mAb or control rat Ig at 50 µg/ml. The suppression of proliferation was not relieved by addition of anti-IFNγ (FIG. 6B).

Example 5 presence of the receptor for IL-12 on murine B cells

To determine whether IL-12 directly affects murine B cell function, we examined peritoneal cells (PeC) for the presence of an IL-12 receptor. The BALB/c mice described in Example 1 were used in these experiments.

Antibodies

The rabbit anti-IL-12 polyclonal antibodies were prepared by Genetics Institute as previously described (Hunter, C. A.,

TABLE

Distribution of peritoneal lymphocytes in IL-12 and control treated mice.

| | DAY 5 | | DAY 7 | | DAY 17 | |
|---|---|---|---|---|---|---|
| | PBS | IL-12 | PBS | IL-12 | PBS | IL-12 |
| Total Cells* | $3.2 \times 10^7$ | $2.3 \times 10^7$ | $1.9 \times 10^7$ | $3.0 \times 10^7$ | $1.5 \times 10^7$ | $1.9 \times 10^6$ |
| Lymphocytes | $2.3 \times 10^6$ | $1.0 \times 10^6$ | $1.7 \times 10^6$ | $1.6 \times 10^6$ | $5.5 \times 10^5$ | $8.2 \times 10^5$ |
| B1 cells | $3.1 \times 10^5$ | $2.1 \times 10^4$ | $3.1 \times 10^5$ | $5.4 \times 10^4$ | $5.7 \times 10^4$ | $1.4 \times 10^4$ |
| B2 cells | $4.4 \times 10^5$ | $8.8 \times 10^4$ | $3.2 \times 10^5$ | $9.9 \times 10^4$ | $7.1 \times 10^4$ | $4.8 \times 10^4$ |
| T cells | $3.7 \times 10^5$ | $6.0 \times 10^5$ | $5.3 \times 10^5$ | $9.6 \times 10^5$ | $1.9 \times 10^5$ | $2.7 \times 10^5$ |

PEC were prepared and stained as described in Materials and Methods. Mice received PBS or 1 µg of IL-12 on days −2, −1, 0, 1, 2 and PC-KLH on day 0. Lymphocytes were gated based on forward and 90° light scatter. B1 cells represent IgM$^+$CD45R$^+$MAC1$^+$ cells and B2 cells represent IgM$^+$CD45R$^+$MAC1$^-$ cells. T cells represent IgM$^-$CD45R$^-$MAC1$^-$ cells that also bear high levels of CD5.
*Numbers represent cells pooled from two mice for each group.

et al., *Infect. Immun.* 62:2818 (1994)). Briefly, animals were immunized subcutaneously with murine IL-12 in CFA and boosted at bi-weekly intervals. Antisera were passed over protein G (Pierce, Rockford, Ill.) using a FPLC system (Pharmacia, Piscataway, N.J.) to isolate immunoglobulins.

Antibodies were coupled to FITC as described in Example 3. For biotinylation of mAbs, 100–500 ug protein in PBS were incubated overnight at 4° C. with a 1/10 volume of 20 mg/ml N-hydroxysuccinimidobiotin in dimethylsulfoxide (Sigma). The Ab mixtures were then passed over PD-10 columns (Pharmacia) to separate conjugated Ab and appropriate fractions were pooled. The conjugates were stored at 4° C. in 0.01% (w/v) sodium azide.

Cell preparations and cultures

Peritoneal cells were removed by injection of 10 ml of HBSS containing 0.1% gelatin. Spleens were removed and single cell suspensions were prepared by passage through wire mesh. For activation with lipopolysaccharide (LPS), spleen cells were incubated at $2 \times 10^5$ cells/well in 96 well microtiter plates (Costar Corning Corp., Cambridge, Mass.) in the presence of 3 µg/ml LPS (from *S. typhimurium*, Westphal, Difco Laboratories, Detroit, Mich.) in RPMI 1640 containing 10% fetal calf serum.

Recombinant murine IL-12 was provided as described in Example 1. Human rIL-12 was purified as described in D'Andrea, A. M., et al., *J. Exp. Med.*, 176:1387 (1992), and had a specific activity of $5.26 \times 10^6$ U/mg. For proliferation assays, murine rIL-12 was added at a final concentration of 50 ng/ml. IL-5 (Genzyme, Corp., Cambridge, Mass.) was used at a concentration of 100 U/ml, and anti-IFNγ (XMG1.2), anti-IL-12, or normal rat Ig were added at 1 ug/ml. Cell cultures were incubated at 37° C. for 48 hr at which time 1 µCi of $^3$HTdR (ICN, Costa Mesa, Calif.) was added. The cells were further incubated for 24 hr and then harvested on glass fiber filters. Radioactivity bound was determined using a Beckman LS 3801 scintillation counter.

Flow cytometry

All flow cytometry was performed on an EPICS ELITE cytometer (Coulter, Hialeah, Fla.) as described in Example 3. Spleen cells and peritoneal cells were prepared as described in Example 3. Spleen cells were analyzed directly or were activated for 72 hr by incubation with 3 ug/ml LPS, 3 ug/ml Con A (Sigma), 10 ug/ml PHA (Sigma) or cultured on 96 well plates coated with 10 ug/ml of anti-CD3 mAb. Fc receptor binding was blocked with 2.4G2 anti-FcγII supernatant (100 ul of supernatant per $10^6$ cells).

IL-12 receptors were detected in a manner similar to that by Desai et al. (Desai, B. B., et al., *J. Immunol.*, 148:3125 (1992). Briefly, cells were incubated with 2.4G2 anti-FcγII supernatant alone or supplemented with 500 nM murine IL-12 for 40 min on ice. For some samples, human rIL-12, murine IL-5, or murine IL-6 (Promega, Madison, Wis.) was also added. Cells were washed and anti-murine IL-12 or rabbit Ig conjugated to biotin was added for 15 min on ice. After washing, mAbs conjugated to FITC and/or phycoerythrin (PE) were added, together with streptavidin-allophycocyanin (Molecular Probes, Eugene, Oreg.). Lymphocytes were gated based on 90° and forward scatter. Further analysis was performed on listmode files using the WinMDI software.

Results

Fresh murine peritoneal cells (FIG. 7A, 7C, and 7E) and spleen cells (FIG. 7B, 7D, and 7F) were examined for IL-12 binding by sequential staining with murine IL-12 followed by biotinylated anti-IL-12 and streptavidin-allophycocyanin. The histograms in FIG. 7 represent CD45 (B220)$^+$ lymphocytes. Fluorescence intensity of anti-IL-12 is shown in the absence of IL-12 (FIG. 7A and 7B) or the presence of 500 nM IL-12 (FIG. 7C and 7D). Fluorescence intensity of normal rabbit Ig-biotin with 500 nM IL-12 was used as a specificity control (FIG. 7E and 7F). Peritoneal cells contained a large population of B cells staining positively for IL-12 binding (FIG. 7C). No staining was observed if IL-12 was omitted (FIG. 7A) or if rabbit Ig-biotin rather than anti-IL12 was used (FIG. 7E). No positive staining was observed with fresh spleen cells under any condition (FIG. 7B, 7D, and 7F).

Figure 8H:
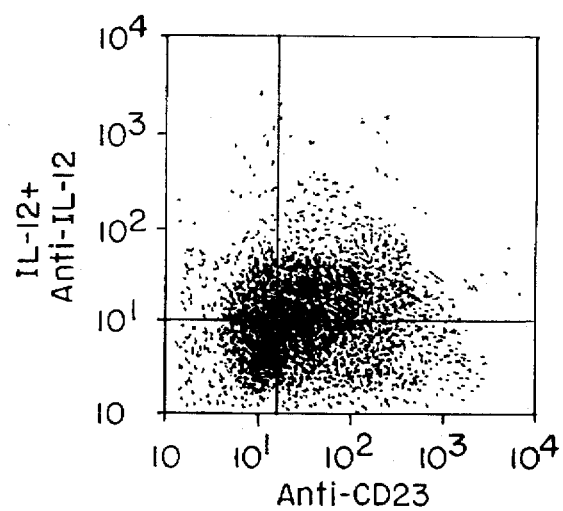
Figure 8I:
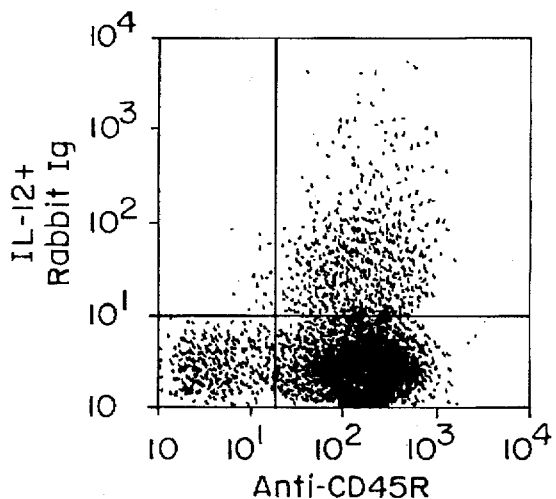
Figure 8J:
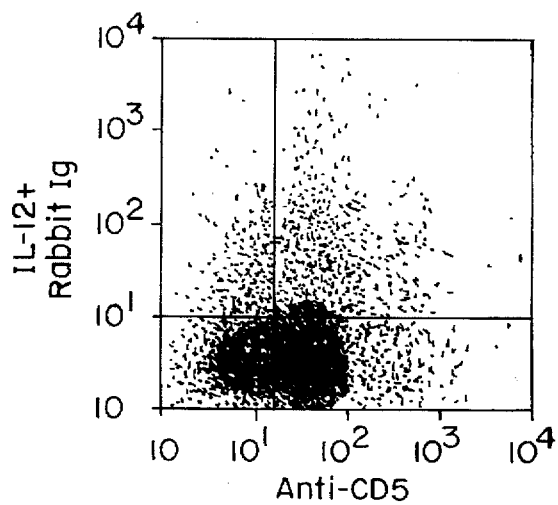
Figure 8K:
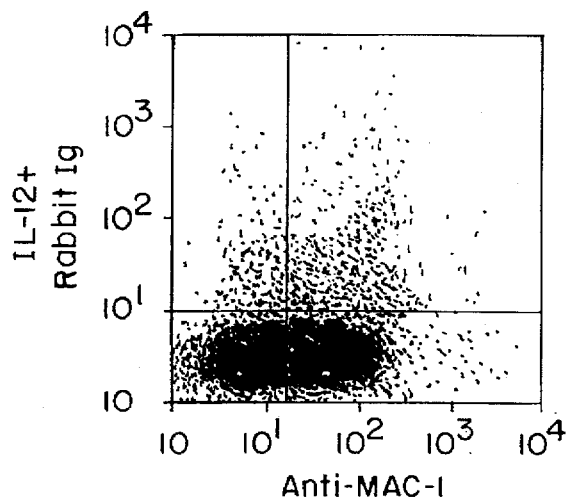

In addition, the subset distribution of the peritoneal B cells that reacted with IL-12 were examined. For this purpose, peritoneal cells were dual stained for IL-12 receptor and various lymphocyte markers: CD45R (FIG. 8A, 8E, and 8I), CD5 (FIG. 8B, 8F, and 8J), MAC-1 (FIG. 8C, 8G, and 8K) or CD23 (FIG. 8D, 8H). The histograms in FIG. 8 represent staining with anti-IL-12 only (FIG. 8A–8D), with 500 nM IL-12 plus anti-IL-12 (FIG. 8E–8H), or with 500 nM IL-12 plus rabbit Ig (FIG. 8I–8K). It was found that both peritoneal B1 (CD45R$^+$, CD5$^\pm$, MAC-1$^+$, CD23$^-$) and B2 (CD45R$^+$, CD5$^-$, MAC-1$^-$, CD23$^+$) lymphocytes bound IL-12. Peritoneal T cells (CD5$^{high}$, CD5R$^-$) however, showed no IL-12 binding. Staining for the IL-12 receptor was again ablated by omitting IL-12 from the procedure or by using normal Ig instead of anti-IL-12 antibody. Thus, both B1 and B2 peritoneal cells constitutively express the IL-12R even though splenic B2 cells do not, indicating a difference in peritoneal and splenic B cell populations.

Figure 9A:
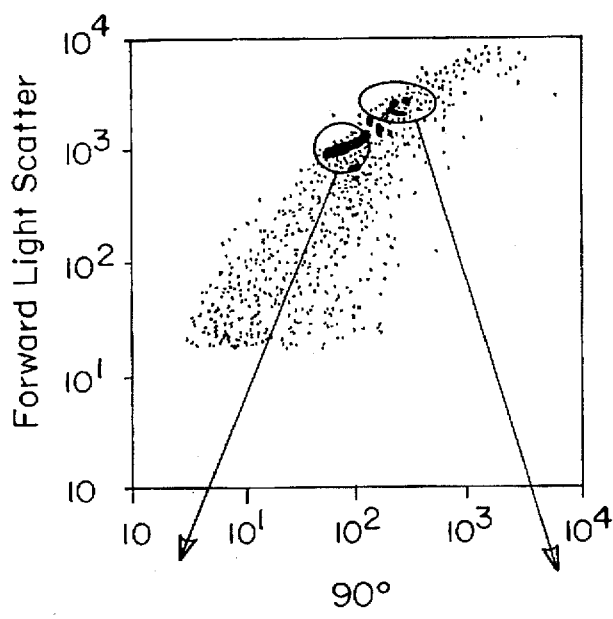
FIGS. 9A is a graph of 90° versus forward light scattering and represents populations of cells present in 3 day cultures.
Figure 9B:
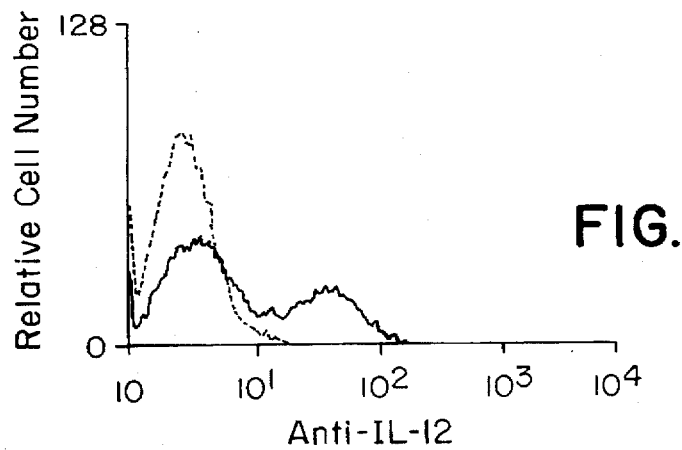
FIGS. 9B–9E are graphs of the fluorescence intensity versus relative cell number of IL-12 binding to lipopolysaccharide (LPS)-activated spleen cells (solid lines indicate the presence of IL-12 during the staining procedure and dashed lines indicate the absence of IL-12).
Figure 9C:
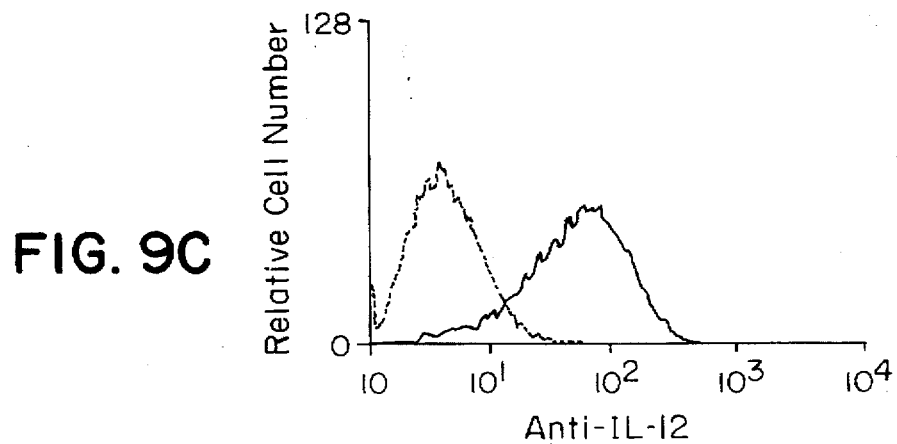
Figure 9D:
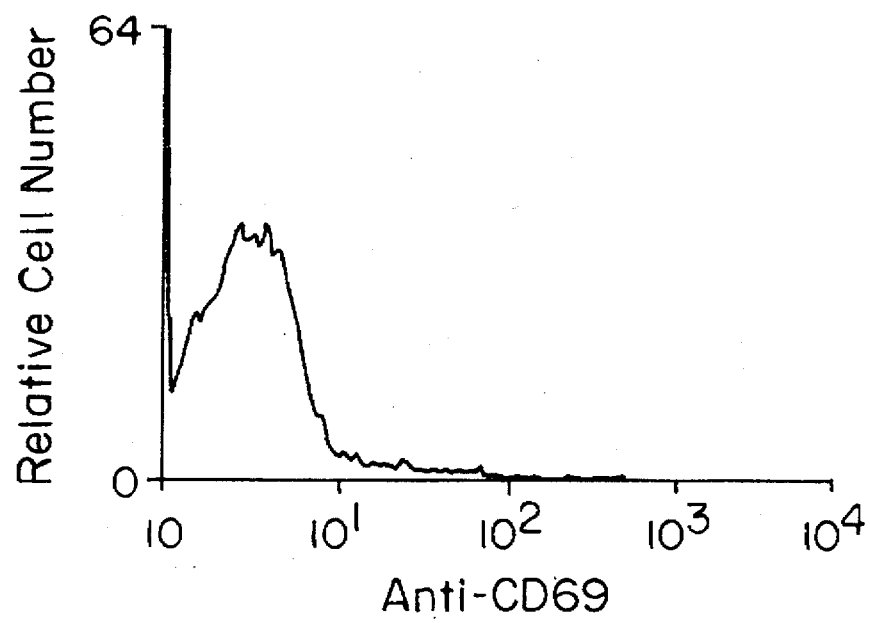
Figure 9E:
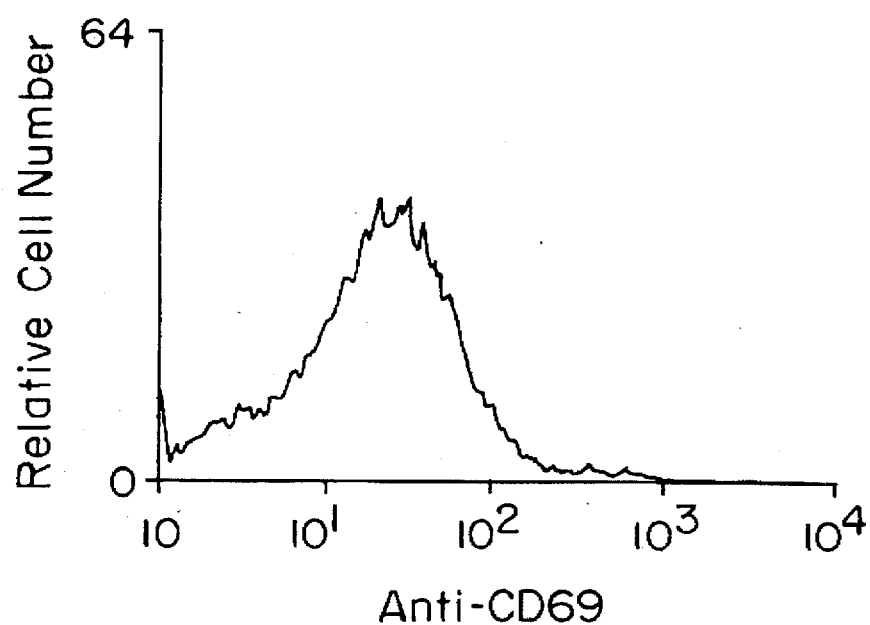

IL-12 receptors in humans can be detected only on activated T cells and NK cells (Desai, B. B., et al., *J. Immunol.*, 148:3125 (1992). Thus, murine spleen cells were cultured with LPS for 72 hr, then stained for IL-12 binding. Two populations were present in the 3-day cultures as determined by 90° and forward light scatter (FIG. 9A). The smaller population (FIG. 9B and 9D) and the larger population (FIG. 9C and 9E) were examined for IL-12 binding (FIG. 9B and 9C). Cells were also examined for CD69 expression (FIG. 9D and 9E). The smaller cells presumably represent an unactivated cell population and larger cells are composed of the blast cell population. The unactivated population exhibited a bimodal staining pattern, while essentially all of the blast cells were positive. Since no staining was observed with fresh spleen cells (FIG. 7), these results indicate that LPS stimulation causes expression of IL-12 receptors on activated blast cells. Staining for CD69, an early marker for T and B cell activation, confirmed that the large cells were in fact activated (FIG. 9D and 9E). All of the IL-12R$^+$ cells were B cells as judged by staining for IgM and CD45R (B220). Surprisingly, no IL-12 binding was detected on T cells activated with Con A or anti-CD3.

Thus, as described above, the presence of an IL-12 receptor (IL-12R) on murine B cell subsets was demonstrated. For this purpose, cells were stained in a three step method using IL-12 followed by biotinylated rabbit anti-mouse IL-12, and streptavidin conjugated to allophycocyanin. Flow cytometric analysis revealed staining of LPS-activated splenic B cells and fresh peritoneal B cells, but no staining of resting splenic B or T cells. Positively stained peritoneal cells included both B220$^+$ CD23$^+$ MAC-1$^+$ (B1) and B220$^+$ CD23$^+$ MAC-1$^+$ (B2) cells. Staining was ablated by the use of biotinylated normal rabbit Ig instead of anti-IL-12, by the use of human IL-12 instead of murine IL-12, or by omitting IL-12 from the procedure. Murine IL-5 or IL-6 did not interfere with staining. Proliferation of PeC in response to IL-5 was suppressed by IL-12, but responsiveness of splenic B cells to LPS stimulation was not inhibited. However, exposure of splenic B cells to anti-IL-12 antibody, in the absence of added IL-12, caused fourfold inhibition of LPS activation. None of the observed effects of IL-12 or anti-IL-12 on B cell activity were reversed by anti-IFNγ antibody. These results indicate that murine B cells bear an IL-12R and while IL-12 directly suppresses peritoneal cells B cell function, it is required for optimal activation of splenic B cells.

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of suppressing B1 cell activity in a host, comprising administering to the host an effective amount of IL-12.

2. A method associated with treating B1 cell activity of a disease involving a B1 cell disorder in a host, comprising administering to the host an effective amount of IL-12.

3. The method of claim 2 wherein the disease involving the B1 cell disorder is an autoimmune disease.

4. The method of claim 3 wherein the autoimmune disease is selected from the group consisting of: systemic lupus erythematosus, rheumatoid arthritis, multiple sclerosis, immune thrombocytopenia purpura, primary Sjogren's syndrome, juvenile arthritis, primary antiphospholipid syndrome, Graves' disease, myasthenia gravis, chronic hepatitis, Crohn's disease and type 1 diabetes.

5. A method of claim 2 wherein the disease involving the B1 cell disorder is selected from the group consisting of: chronic lymphocytic leukemia, hairy cell leukemia, prolymphocytic leukemia, well differentiated lymphocytic lymphomas infection with, human immunodeficiency virus, infectious mononucleosis and schizophrenia.

6. A method of assessing the ability of a substance to suppress IL-12 inhibition of B1 cell activity, comprising the steps of:

a) combining the substance with cultured B1 cells and IL-12, under conditions appropriate for IL-12 inhibition of B1 cell activity; and b) assessing whether inhibition of B1 cell activity results, wherein activation of B1 cell activity is an indication that the substance suppresses IL-12 inhibition of B1 cell activity.

7. A method of assessing the ability of a substance to enhance IL-12 inhibition of B1 cell activity, comprising the steps of:

a) combining the substance with cultured B1 cells and IL-12, under conditions appropriate for inhibition of B1 cell activity; and b) assessing whether enhancement of B1 cell activity results, wherein an increase in the inhibition of B1 cell activity above that observed in the presence of IL-12 is an indication that the substance interferes with B1 cell activity.

* * * * *